(12) United States Patent
Kent et al.

(10) Patent No.: US 9,511,231 B1
(45) Date of Patent: Dec. 6, 2016

(54) SYSTEMS AND METHODS FOR RECORDING EVOKED RESPONSES FROM NEUROSTIMULATION

(71) Applicant: Pacesetter, Inc., Sunnyvale, CA (US)

(72) Inventors: Alexander Kent, Mountain View, CA (US); Edward Karst, Los Angeles, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/715,262

(22) Filed: May 18, 2015

(51) Int. Cl.
*A61N 1/00* (2006.01)
*A61N 1/36* (2006.01)
*A61N 1/05* (2006.01)

(52) U.S. Cl.
CPC ......... *A61N 1/36139* (2013.01); *A61N 1/0551* (2013.01)

(58) Field of Classification Search
CPC .......................... A61N 1/36139; A61N 1/0551
See application file for complete search history.

(56) References Cited

U.S. PATENT DOCUMENTS

| 8,868,188 B2 * | 10/2014 | Hershey | ................... A61N 1/36 607/30 |
| 2011/0054565 A1 | 3/2011 | Wacnik et al. | |
| 2014/0236257 A1 * | 8/2014 | Parker | ................ A61B 5/04001 607/46 |

FOREIGN PATENT DOCUMENTS

WO    2006029257 A2    3/2006

* cited by examiner

*Primary Examiner* — George Manuel
(74) *Attorney, Agent, or Firm* — Theresa A. Raymer

(57) ABSTRACT

Systems and methods for closed loop spinal cord stimulation are provided. The systems and methods position a first electrode proximate to a dorsal column. The first electrode is electrically coupled to an implantable pulse generator (IPG). The systems and methods further program the IPG to deliver excitation pulses to the first electrode based on a stimulation level. The excitation pulses are emitted from the first electrode. The systems and methods further position a second electrode proximate to a dorsal root. The second electrode is electrically coupled to the IPG. The systems and methods further measure at the second electrode a first evoked potential waveforms resulting from the excitation pulses.

17 Claims, 13 Drawing Sheets

SYSTEMS AND METHODS FOR RECORDING EVOKED RESPONSES FROM NEUROSTIMULATION

BACKGROUND OF THE INVENTION

Embodiments of the present disclosure generally relate to neurostimulation (NS) systems, and more particularly to systems and methods for recording evoked potentials resulting from NS for closed loop spinal cord stimulation.

NS systems are devices that generate electrical pulses and deliver the pulses to nerve tissue to treat a variety of disorders via one or more electrodes. For example, SCS has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses depolarize neurons and generate propagating action potentials into certain regions or areas of nerve tissue. The propagating action potentials effectively mask certain types of physiological neural activity, increase the production of neurotransmitters, or the like. For example, applying electrical energy to the spinal cord associated with regions of the body afflicted with chronic pain can induce "paresthesia" (a subjective sensation of numbness or tingling) in the afflicted bodily regions. Inducing this artificial sensation replaces the feeling of pain in the body areas effectively masking the transmission of non-acute pain sensations to the brain.

During stimulation by the NS systems, evoked potentials are emitted from the stimulated nerve tissue. The evoked potential signals may be generated by neuronal transmembrane currents of neurons activated following or in response to the NS. The simultaneous activation of multiple neurons generates a signal of sufficient amplitude for recording. The evoked potential signals propagate within the population of sensory nerve fibers through subsequent orthodromic or antidromic propagation from the excitation site. It has been proposed that the NS system may measure the evoked potential for a feedback mechanism to adjust the NS.

However, the evoked potential signals are measured proximate to the source of the NS, specifically, the electrodes of the NS system near the dorsal column. Due to the proximity, the evoked potential signal includes stimulation artifacts corresponding to the NS emitted by the electrodes. Further, the evoked potential signal measured at the dorsal column primarily corresponds to the excitation of the sensory Aβ fibers, since the Aδ and C fibers indicating pain travel in a different pathway located away from the dorsal column. Moreover, the thickness of the cerebrospinal fluid around the dorsal column reduces the evoked potential signal. A need exists to overcome the shortcomings of traditional recording locations of the evoked potential signal.

SUMMARY

In accordance with one embodiment, a method for closed loop spinal cord stimulation is provided. The method includes positioning a first electrode proximate to a dorsal column. The first electrode is electrically coupled to an implantable pulse generator (IPG). The method further includes programming the IPG to deliver excitation pulses to the first electrode based on a stimulation level. The excitation pulses are emitted from the first electrode. The method includes positioning a second electrode proximate to a dorsal root. The second electrode is electrically coupled to the IPG. The method further measuring at the second electrode a first evoked potential waveforms resulting from the excitation pulses.

In an embodiment, a system for closed loop spinal cord stimulation is provided. The system includes an implantable pulse generator (IPG) electrically coupled to a first electrode positioned proximate to a dorsal column. The IPG is configured to deliver excitation pulses to the first electrodes based on a stimulation level. The system also includes sensing circuitry of the IPG of electrically coupled to a second electrode positioned proximate to a dorsal root. The sensing circuitry is configured to measure a first evoked potential waveform at the second electrode resulting from the excitation pulses.

DETAILED DESCRIPTION

Figure 1:
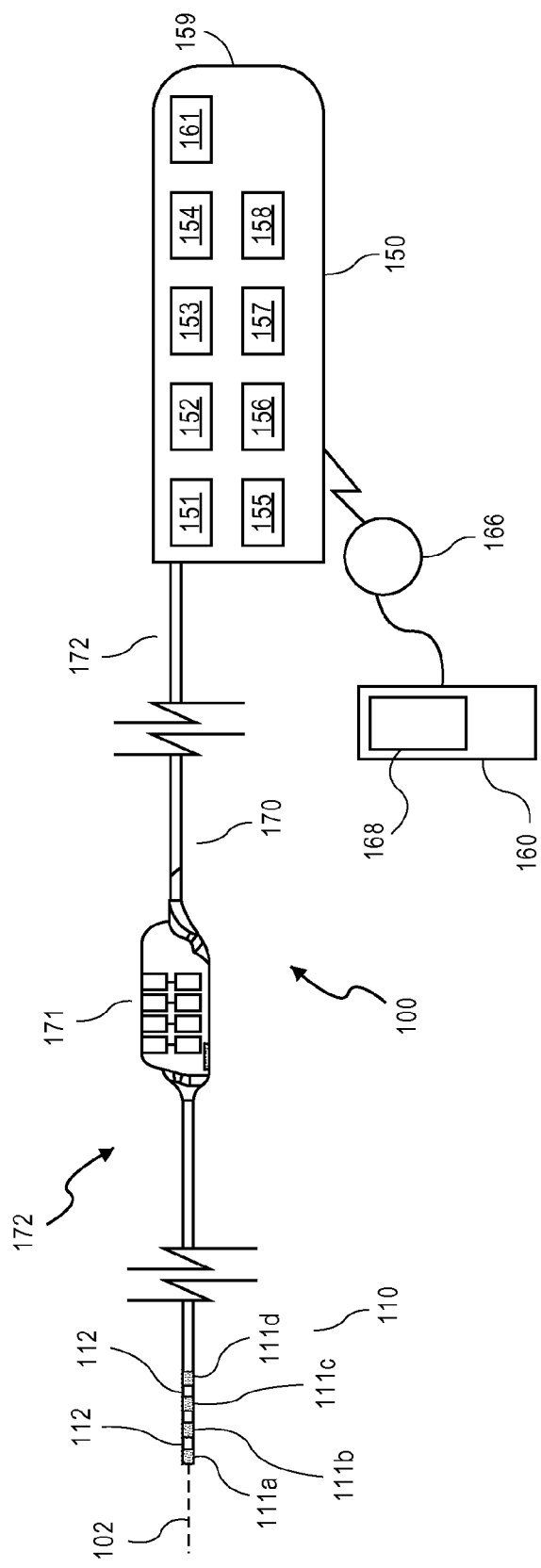
FIG. 1 is illustrates a neurostimulation system, according to an embodiment of the present disclosure.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

Various embodiments described herein include a method and/or system for a closed loop spinal cord stimulation based on a novel approach for recording evoked potential waveforms at or proximate to the dorsal root (DR). For example, the evoked potential waveforms may be recorded from the cell bodies of the dorsal root ganglion (DRG), spinal nerve, or the like. The recorded evoked potential waveforms may include neural activity of the Aβ sensory fibers carrying non-painful sensory information to the spinal cord, and Aδ and C sensory fibers carrying information about painful stimuli. The activation of the sensory fibers may correspond to one or more characteristics of the morphology of the recorded evoked potential waveform.

In various embodiments the recorded evoked potential waveform may be used to adjust the NS parameters to maintain sufficient activation of the appropriate types of neural elements. For example, based on the morphology of the evoked potential waveform, the NS parameters may be adjusted to increase an amplitude corresponding to the activation of the Aβ sensory fibers. Optionally, based on the morphology of the recorded evoked potential appropriate stimulation parameter ranges (i.e. minimum and maximum stimulation amplitude) may be determined corresponding to a therapeutic window. The recorded evoked potential waveforms may be recorded from contacts present on a stimulation lead, including a DRG lead or percutaneous lead with tip steered into the dorsal root area, or on a plurality of leads. For example, a stimulation lead proximate to the dorsal column (DC) and a DRG lead.

A technical effect of the various embodiments herein improve recording fidelity of the evoked potential waveform due to the smaller intradural space of the DR between the lead and the neurons, and the reduced motion of the recording lead with changes in posture. A technical effect of the various embodiments herein allow precise identification of areas affected by the NS based on the recording of the evoked potential waveform at the DR that is specific to a particular dermatome, which allow for precise identification of the areas affect by the SCS. A technical effect of the various embodiments herein allow patients to remain under general anesthesia during intraoperative placement of a lead. A technical effect of the various embodiments herein provides a means to objectively quantify the effect of SCS on a patient rather than relying on subjective descriptions from the patient.

FIG. 1 depicts an NS system 100 that generates electrical pulses (e.g., excitation pulses) for application to tissue of a patient according to one embodiment. For example, the NS system 100 may be adapted to stimulate spinal cord tissue, dorsal root, dorsal root ganglion, peripheral nerve tissue, deep brain tissue, cortical tissue, cardiac tissue, digestive tissue, pelvic floor tissue, or any other suitable nerve tissue of interest within a patient's body.

The NS system 100 includes an implantable pulse generator (IPG) 150 that is adapted to generate electrical pulses for application to tissue of a patient. The IPG 150 typically comprises a metallic housing or can 159 that encloses a controller 151, pulse generating circuitry 152, a charging coil 153, a battery 154, a far-field and/or near field communication circuitry 155, battery charging circuitry 156, switching circuitry 157, sensing circuitry 158, memory 161, and the like. The controller 151 typically includes a microcontroller or other suitable processor for controlling the various other components of the device. Software code may be stored in memory 161 of the IPG 150 or integrated with the controller 151 for execution by the microcontroller or processor to control the various components of the device.

The IPG 150 may comprise a separate or an attached extension component 170. If the extension component 170 is a separate component, the extension component 170 may connect with a "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within the connector portion 171 or within the IPG header for electrical connection with respective connectors. Thereby, the pulses originating from the IPG 150 are provided to the one or more leads 110. The pulses are then conducted through the conductors of the lead 110 and applied to tissue of a patient via electrodes 111a-d. Any suitable known or later developed design may be employed for connector portion 171.

The electrodes 111a-d may be positioned along a horizontal axis 102 of the lead 110, and are angularly positioned about the horizontal axis 102 so the electrodes 111a-d do not overlap. The electrodes 111a-d may be in the shape of a ring such that each electrode 111a-d continuously covers the circumference of the exterior surface of the lead 110. Each of the electrodes 111a-d are separated by non-conducting rings 112, which electrically isolate each electrode 111a-d from an adjacent electrode 111a-d. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The electrodes 111a-d may be configured to emit the pulses in an outward radial direction proximate to or within a stimulation target. The electrodes 111a-d may also be configured to acquire electrical potential measurements (e.g., voltage, current) for the sensory circuit 158, such as evoked potentials emitted from the stimulation target.

Optionally, the IPG 150 may have more than one lead 110 connected via the connector portion 171 of the extension component 170 or within the IPG header. For example, a DRG stimulator, a steerable percutaneous lead, and/or the like. Additionally or alternatively, the electrodes 111a-d of each lead 110 may be configured separately to emit excitation pulses or measure the evoked potential emitted from the stimulation target.

Additionally or alternatively, the electrodes 111a-d may be in the shape of a split or non-continuous ring such that the pulse may be directed in an outward radial direction adjacent to the electrodes 111a-d. Examples of a fabrication process of the electrodes 111a-d is disclosed in U.S. patent application Ser. No. 12/895,096, entitled, "METHOD OF FABRICATING STIMULATION LEAD FOR APPLYING ELEC- TRICAL STIMULATION TO TISSUE OF A PATIENT," which is expressly incorporated herein by reference.

It should be noted the electrodes 111a-d may be in various other formations, for example, in a planar formation on a paddle structure as disclosed in U.S. Provisional Application No. 61/791,288, entitled, "PADDLE LEADS FOR NEUROSTIMULATION AND METHOD OF DELIVERYING THE SAME," which is expressly incorporated herein by reference.

The lead 110 may comprise a lead body 172 of insulative material about a plurality of conductors within the material that extend from a proximal end of lead 110, proximate to the IPG 150, to its distal end. The conductors electrically couple a plurality of the electrodes 111a-d to a plurality of terminals (not shown) of the lead 110. The terminals are adapted to receive electrical pulses and the electrodes 111a-d are adapted to apply the pulses to the stimulation target of the patient. Also, sensing of physiological signals may occur through the electrodes 111a-d, the conductors, and the terminals. It should be noted that although the lead 110 is depicted with four electrodes 111a-d, the lead 110 may include any suitable number of electrodes 111a-d (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for all embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

For implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different pulses on different electrodes 111a-d may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various electrodes of one or more leads 111a-d as is also known in the art. Various sets of parameters may define the pulse characteristics and pulse timing for the pulses applied to the various electrodes 111a-d as is known in the art. Although constant excitation pulse generating circuitry is contemplated for some embodiments, any other suitable type of pulse generating circuitry may be employed such as constant voltage pulse generating circuitry.

The sensing circuitry 158 may measure an electric potential (e.g., voltage, current) over time of proximate tissue, such as the DRG or DR, through at least one of the electrodes 111 and configured to measure the electrical potential. For example, the sensing circuitry 158 may measure an evoked potential waveform from the neurons of the DRG or DR resulting from the excitation pulses emitted for the NS. The sensing circuitry 158 may include amplifiers, filters, analog to digital converters, memory storage devices, digital signal processors or the like. Optionally, the sensing circuitry 158 may store the electric potential in the memory 161.

An external device 160 may be implemented to charge/recharge the battery 154 of the IPG 150 (although a separate recharging device could alternatively be employed), to access the memory 161, and to program the IPG 150 on the pulse specifications while implanted within the patient. Although, in alternative embodiments separate programmer devices may be employed for charging and/or programming the NS system 100. The external device 160 may be a processor-based system that possesses wireless communication capabilities. Software may be stored within a non-transitory memory of the external device 160, which may be executed by the processor to control the various operations of the external device 160. A "wand" 165 may be electrically connected to the external device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IPG 150.

The user may initiate communication with the IPG 150 by placing the wand 165 proximate to the NS system 100. Preferably, the placement of the wand 165 allows the telemetry system of the wand 165 to be aligned with the far-field and/or near field communication circuitry 155 of the IPG 150. The external device 160 preferably provides one or more user interfaces 168 (e.g., display, touchscreen, keyboard, mouse, buttons, or the like) allowing the user to operate the IPG 150. The external device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different electrode 111a-d combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference. Optionally, the user interface 168 may permit the user to designate which electrodes 111a-d are to stimulate (e.g., emit excitation pulses, in an anode state, in a cathode state) the stimulation target, to measure the evoked potential (e.g., connecting to the sensing circuitry 158) resulting from the excitation pulses, remain inactive (e.g., floating), or the like. Additionally or alternatively, the external device 160 may access or download the electrical measurements from the memory 161 acquired by the sensing circuitry 158.

Also, the external device 160 may permit operation of the IPG 150 according to one or more spinal cord stimulation (SCS) programs or therapies to treat the patient. For example, the SCS program corresponds to the SCS delivered and/or executed by the IPG 150. Each SCS program may include one or more sets of stimulation parameters of the pulses including pulse amplitude, stimulation level, pulse width, pulse frequency or inter-pulse period, pulse repetition parameter (e.g., number of times for a given pulse to be repeated for respective stimset during execution of program), biphasic pulses, monophasic pulses, etc. The IPG 150 may modify its internal parameters in response to the control signals from the external device 160 to vary the stimulation characteristics of the stimulation pulses transmitted through the lead 110 to the tissue of the patient. NS systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

Figure 2:
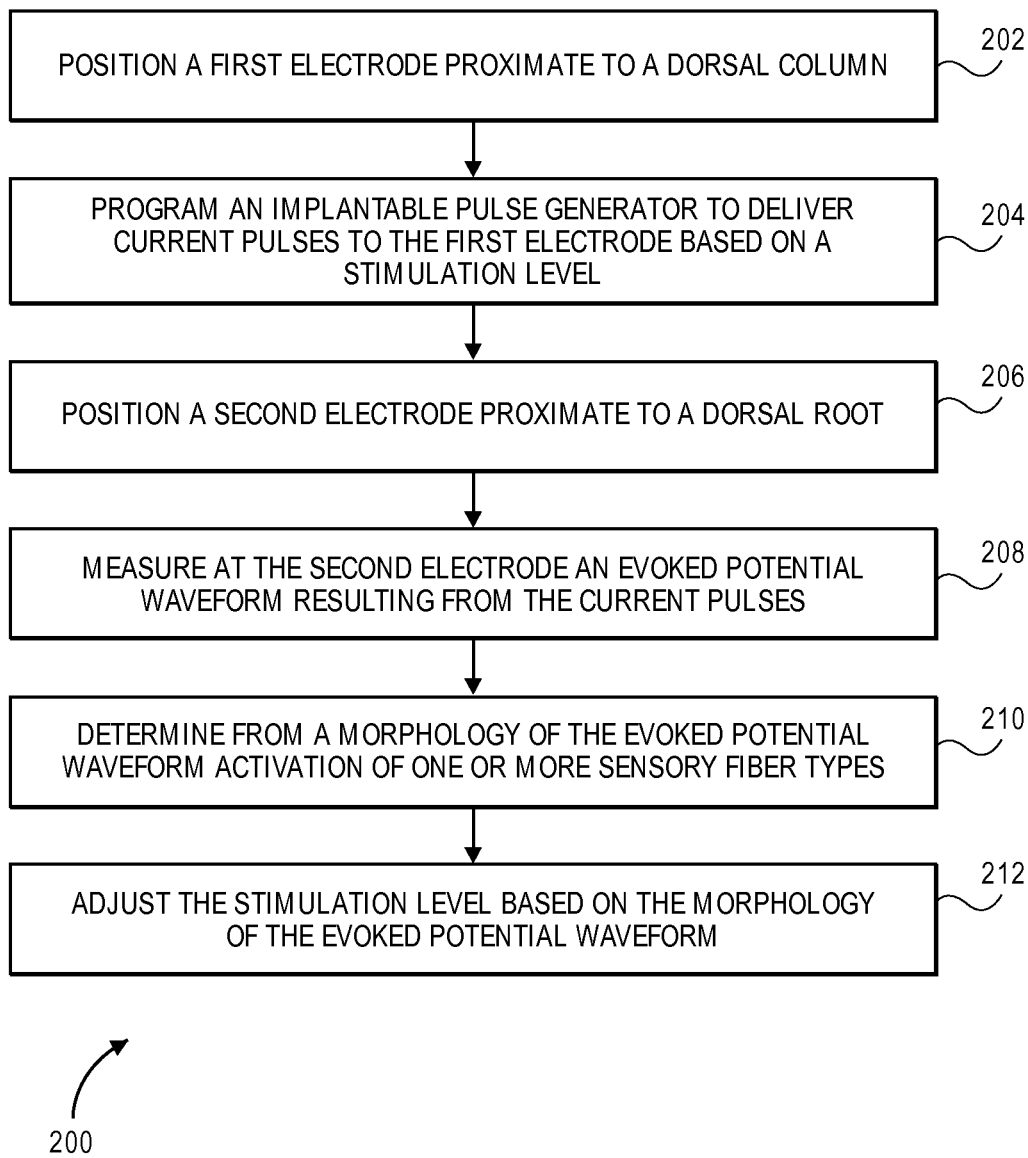
FIG. 2 is a flowchart of a method for closed loop spinal cord stimulation, according to an embodiment of the present disclosure

FIG. 2 is a flowchart of a method 200 for a closed loop spinal cord stimulation based on recorded evoked potential waveforms measured proximate to the DR. The method 200 may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of a closed loop signal determining and/or adjusting one or more stimulation parameters based on a measured evoked potential waveform. It should be noted, other methods may be used, in accordance with embodiments herein.

One or more methods may (i) position a first electrode proximate to a dorsal column, (ii) program the IPG to deliver excitation pulses to the first electrode based on a stimulation level, (iii) position a second electrode proximate to a DR, and (iv) measure, at the second electrode, a first evoked potential waveform resulting from the excitation pulses.

Figure 3:
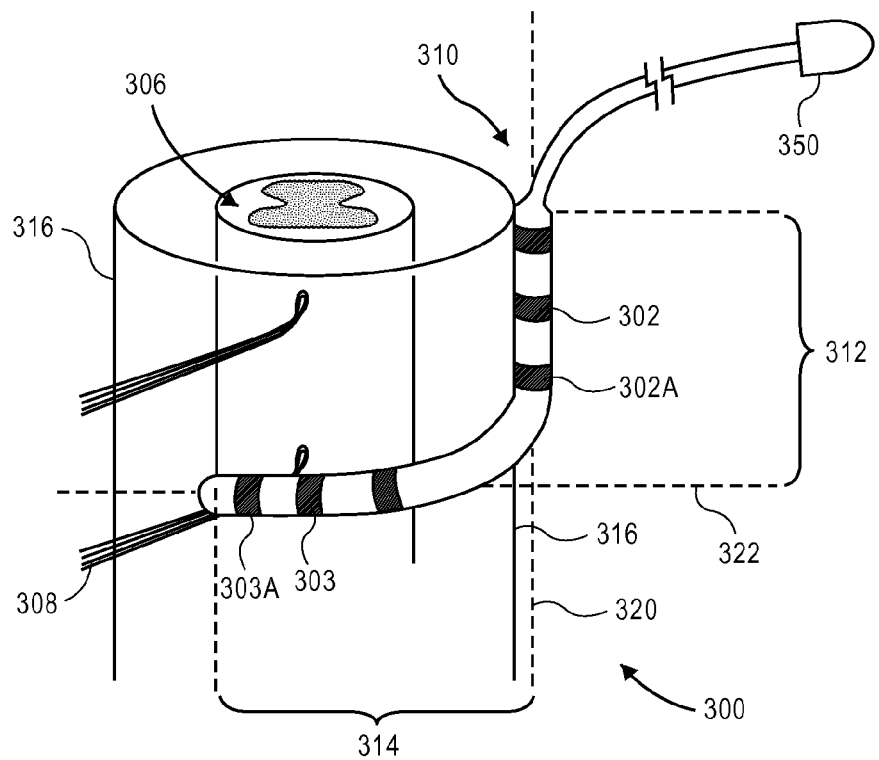
FIG. 3 illustrates a lead placement for spinal cord stimulation of a patient, according to an embodiment of the present disclosure

Beginning at 202, a first electrode (e.g., 302a) is positioned proximate to a dorsal column (DC) 306. FIG. 3 is an illustration of a lead placement 300, in accordance with an embodiment. The lead 310 is configured to flex such that a first portion 312 of the lead 310 may extend parallel to the DC 306 along an axis 320, and a second portion 314 may extend along a DR 308 parallel to an axis 322.

The first portion 312 of the lead 310 may be positioned at a target position within an epidural space of a patient so as to be in close proximity to a nerve tissue of interest along the DC 306. The lead 310 includes a plurality of electrodes that form a first and second series of electrodes 302 and 303 overlaid on the surface of the lead 310. The first series of electrodes 302 may be proximate and/or adjacent to a dura layer 316 of the DC 306. For example, the electrode 302a may be located immediately adjacent to the DC 306, such as within 3 mm of the DC 306. In another example, the electrode 302a may be no more than 10 mm from the DC 306. The first series of electrodes 302 are electrically coupled to an IPG 350. The IPG 350 may be similar to and/or identical to the IPG 150 shown in FIG. 1.

The second series of electrodes 303 may be proximate to and/or adjacent to the epidural space of the DR 308. For example, the electrode 303a may be located immediately adjacent to the DR 308, such as within 3 mm of the DR 308. In another example, the electrode 303a may be no more than 10 mm from the DR 308. The DR 308 may correspond to a particular or select dermatome to be stimulated by the IPG 350 based on the SCS program. The second series of electrodes 303 are electrically coupled to the sensing circuitry of the IPG 350, which allow the IPG 350 to identify whether the stimulation target (e.g., the select dermatome) is affected by the excitation pulses. For example, the second series of electrodes 303 may enable the lead 310 to have a multi-contact array of multiple electrode pairs to detect propagation of the evoked potentials generated by one or more sensory fibers in response to the excitation pulses.

It should be noted that in other embodiments, the lead 310 may include a curved paddle structure having an array of electrodes along a front surface of the lead such that a first portion of the array of electrodes are proximate to the dura layer 316 near DC 306 and a second portion of the array of electrodes are proximate to the DR 308.

Figure 4:
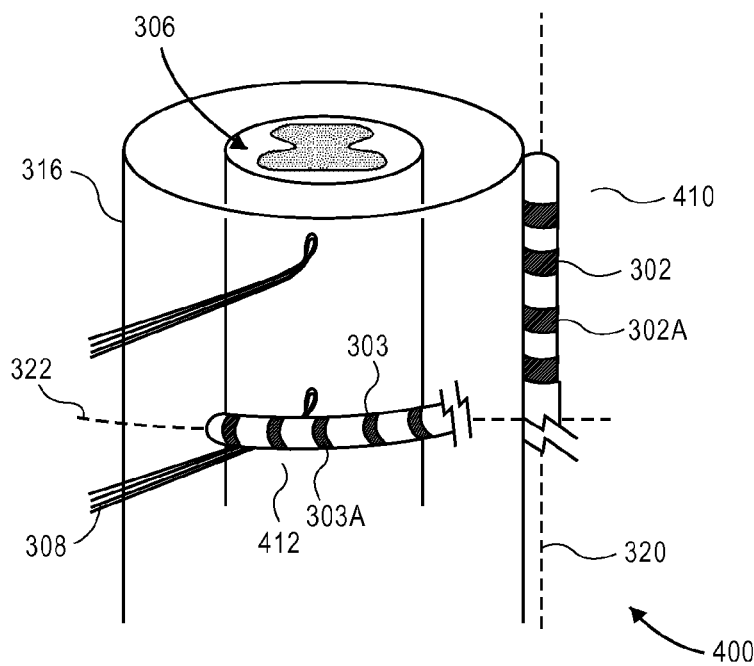
FIG. 4 illustrates a placement of a first lead and a second lead for spinal cord stimulation of a patient, according to an embodiment of the present disclosure.

Optionally, the IPG 350 may be coupled to a first lead 410 and/or a second lead 412. FIG. 4 illustrates a placement of the first lead 410 and the second lead 412, in accordance with an embodiment. The first lead 410 and the second lead 412 may be coupled to the IPG 350, for example, by a connector portion (e.g., the connector portion 171 of FIG. 1)

The first lead 410 may be positioned at a target position within an epidural space of a patient so as to be in close proximity to a nerve tissue of interest along the DC 306 extending along the axis 320. The first lead 410 may include the first series of electrodes 302 that are electrically coupled to the IPG 350. The second lead 412 may extend along the DR 308 parallel to the axis 322. The second lead 412 may include the second series of electrodes 303 that are electrically coupled to the sensing circuitry of the IPG 350.

In at least one embodiment, additional leads may be coupled to the IPG 350. For example, an additional lead may extend along another DR corresponding to a dermatome not intended to be stimulated by IPG 350, based on the SCS program. Additionally or alternatively, the additional lead may extend along another DR corresponding to an additional dermatome intended to be stimulated by the IPG 350 based on the SCS program.

Additionally or alternatively, in at least one embodiment the IPG 350 may not be coupled to a lead (e.g., the first lead 410) positioned proximate to the DC 306. For example, the IPG 350 may be coupled to the second lead 412 and/or additional leads proximate to the DR 308 or DRG.

At 204, program the IPG 150 to deliver excitation pulses to the first electrode (e.g., 302a) based on a stimulation level. The stimulation level may correspond to an amplitude, frequency, pulse width, and/or the like of the excitation pulses. The stimulation levels may be defined by the SCS program. For example, the IPG 350 may be programmed or receive the SCS program from an external device (e.g., the external device 160). The SCS program may define one or more stimulation levels that correspond to different simulation waveforms formed by the excitation pulses, such as a burst stimulation waveform, a tonic stimulation waveform, a biphasic pulse, or the like which are emitted from at least one of the first series of electrodes 302.

For example, the excitation pulses may be delivered by the IPG 350 to the electrode 302a. The excitation pulses are emitted from the electrode 302a in an outward direction towards a stimulation target within the DC 306. The excitation pulses may be repeatedly emitted by the electrode 302a based on the SCS program.

Additionally or alternatively, the excitation pulses may be emitted from the first series of electrodes 302 and/or the second series of electrodes 303. For example, the excitation pulses may be delivered by the IPG 350 to the electrode 303a. The excitation pulses are emitted from the electrode 303a in an outward direction towards a stimulation target, such as, the DR 308 and/or DRG. In another example, the excitation pulses may be delivered by the IPG 350 to the electrodes 302a and 303a.

Figure 5:
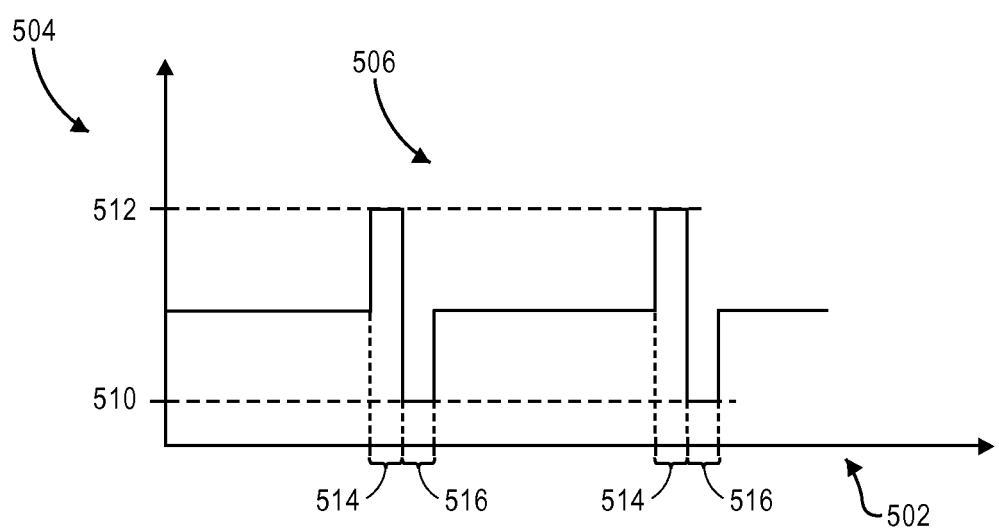
FIG. 5 illustrates a graphical representation of excitation pulses delivered to an electrode based on a spinal cord stimulation program, according to an embodiment of the present disclosure.

FIG. 5 illustrates a series of excitation pulses 506 delivered by the IPG 350 and emitted by one or more of the first series of electrodes 302 (e.g., the electrode 302a) and/or one or more of the second series of electrodes 303 (e.g., the electrode 303a) of FIGS. 3 and 4 at a predetermined amplitude (e.g., a positive amplitude 512, a negative amplitude 510) and duration 514, 516 in accordance with an embodiment. A horizontal axis 502 represents time, and a vertical axis 504 may represent voltage, electrical potential, or current. The excitation pulses 506 form a stimulation waveform based on the SCS program, such as a tonic or burst stimulation waveform.

It should be noted that in other embodiments the excitation pulses 506 may form other stimulation waveforms (e.g., burst stimulation waveform). It should be noted that although the amplitudes 510 and 512 are shown being equal in magnitude, in alternative embodiments the amplitudes 510 and 512 may not equal. For example, the positive amplitude 512 may have a greater amplitude than the negative amplitude 510.

It should be noted that although the durations 514 and 516 of the excitation pulses 506 are shown being equal in length (e.g., pulse width), in alternative embodiments the durations 514 and 516 may not be equal. For example, the duration 514 of the excitation pulse 506 corresponding to the positive amplitude 512 may be longer or shorter in length (e.g., pulse width) than the duration 516 of the excitation pulse 506 corresponding to the negative amplitude 510.

Figure 6:
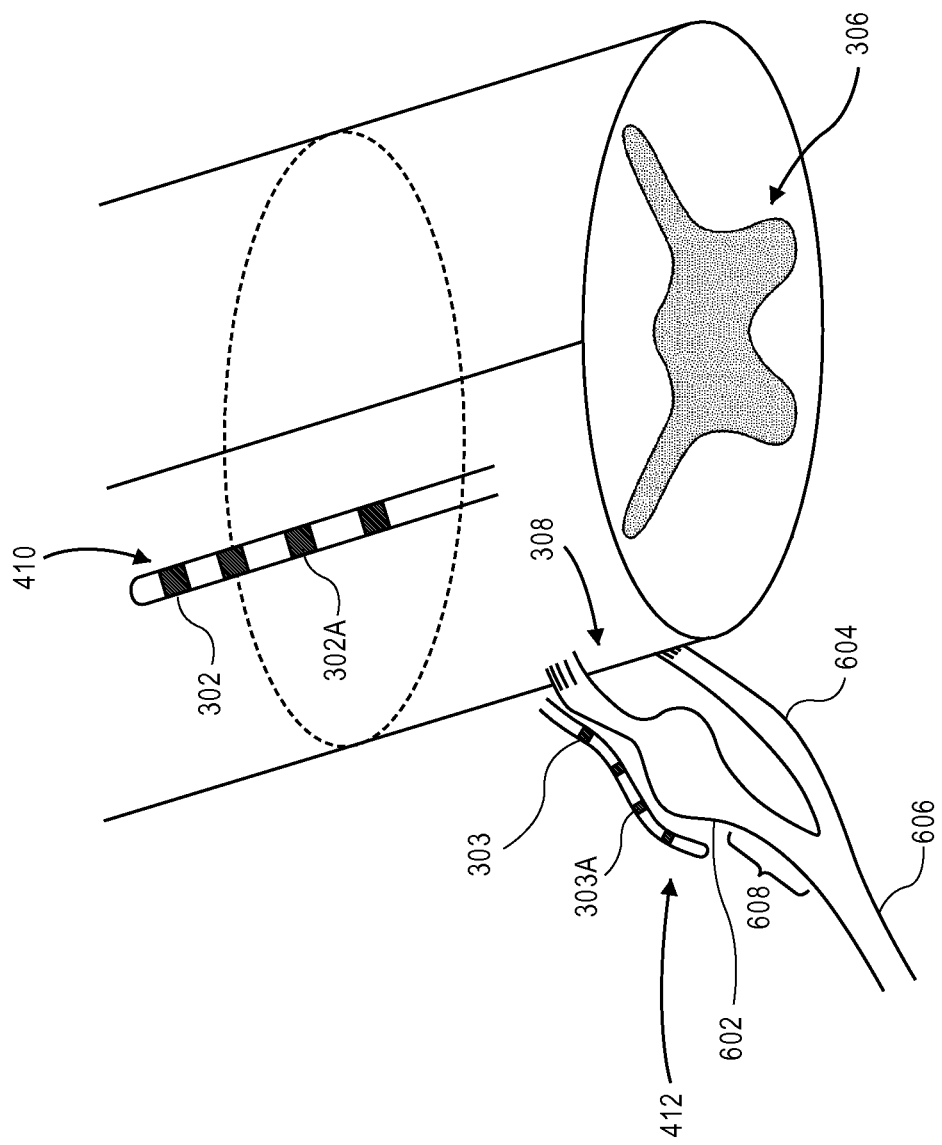
FIG. 6 illustrates an alternative view of the placement shown in FIG. 4.

At 206, a second electrode (e.g., 303a) is positioned proximate to the DR 308. FIG. 6 is an alternative view of the lead placement shown in FIG. 4. FIG. 6 illustrates an electrode 303a of the lead 412 positioned proximate to the DR 308, or particularly, to cell bodies (e.g., soma) of the DRG 602. The DR 308 is further illustrated meeting with the ventral root 604 at a spinal nerve 606. The DR 308 contains afferent or sensory nerve fibers such as the Aβ sensory fiber, the Aδ sensory fiber, and the C sensory fiber that correspond to a select or particular dermatome intended to be stimulated by the SCS program. The ventral root 604 contains efferent or motor nerve fibers. The spinal nerve 606, which branches into the DR 308 and the ventral root 604, includes both the afferent nerve fibers (e.g., Aβ sensory fiber, the Aδ sensory fiber, the C sensory fiber) and efferent nerve fibers (e.g., motor fibers).

The electrodes 303 may be positioned adjacent to the epidural space of the DR 308, such that the intradural space is between the DR 308 and the electrodes 303. The position of the second series of electrodes 303 of the lead 412 enable one or more of the electrodes 303 (e.g., the electrode 303a) to detect and/or measure the evoked potentials generated by one or more of the Aβ sensory, Aδ sensory, and/or C sensory fibers in response to the excitation pulses 506 emitted from the electrode 302a. For example, the second series of electrodes 303 are positioned along a travel path of the antidromic propagation of the evoked potential generated by the one or more of the Aβ sensory, Aδ sensory, and/or C sensory fibers. The travel path may include the cell bodies of the DRG 308 to the spinal nerve 606 along the axon 608.

In various embodiments, the electrode 303a of the lead 412 may be positioned in other locations proximate to the DR 308 other than the DRG 308 as shown in FIG. 6. For example, the electrode 303a may be positioned adjacent to the spinal nerve 606. In another example, the electrode 303a may be positioned along the axon 608 between the spinal nerve 606 and the DRG 308. Additionally or alternatively, the one or more of electrodes 303 may be positioned at and/or proximate to the spinal nerve 606 to detect and/or measure the evoked potentials generated by one or more of the afferent nerve fibers concurrently or simultaneously with action potentials generated by the efferent nerve fibers.

Figure 7:
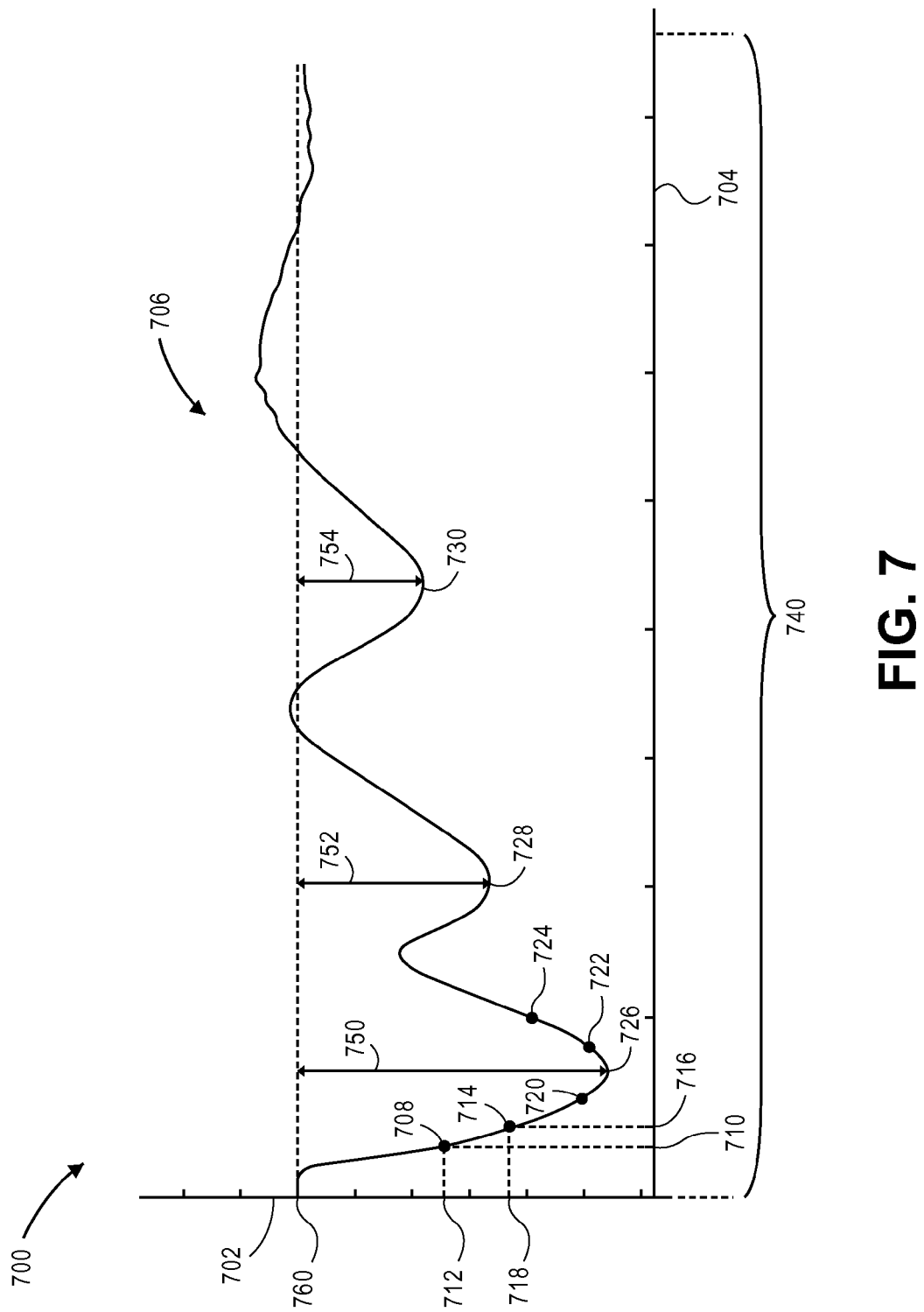
FIG. 7 illustrates a graphical representation of electrical potential measurements at an electrode, in accordance with an embodiment.

At 208, measure at the second electrode (e.g., 303a) an evoked potential waveform 706 resulting from the excitation pulses 506. FIG. 7 illustrates a graphical representation 700 of electrical potential measurements at the electrode 303a proximate to the cell bodies of the DRG 602. A horizontal axis 704 represents time, and a vertical axis 702 represents a voltage of sensed electrical potentials measured at the electrode 303a. The electrical potential measurements correspond to an electrical potential (e.g., voltage) at the electrode 303a measured by the sensing circuitry 158. The electrical potential measurements form an evoked potential waveform 706 resulting from the excitation pulses 506, which are measured by the sensing circuitry 158 at the electrode 303a.

For example, during intraoperative placement or implantation of the lead (e.g., the lead 310, the leads 410, 412), under general anesthesia, the clinician may instruct the IPG 350 to emit excitation pulses for intraoperative targeting of the lead. The IPG 350 may instruct the electrode 302a to emit the excitation pulses 506 towards neurons corresponding to a select dermatome (e.g., the stimulation target) within the DC 306. The excitation pulses 506 may generate evoked potentials within the neurons along one or more sensory fibers corresponding to the select dermatome. The evoked potentials travel along the sensory nerve fibers during subsequent antidromic propagation towards the electrode 303a positioned proximate to the DR 308 corresponding to the select dermatome. The electrical characteristics (e.g., voltage, current) of the evoked potentials may adjust and/or change the electrical potential at and/or proximate to the electrode 303a. The sensing circuitry 158, electrically coupled to the electrode 303a, may measure and/or detect the evoked potentials corresponding to the change in electrical potential over time at the electrode 303a at a sampling and/or acquisition frequency. The sampling frequency may correspond to a number of electrical potential measurements the sensing circuitry 158 may measure over time. The electrical potential measurements or evoked potential recordings are shown plotted over time in the graphical representation 700, forming the evoked potential waveform 706.

Optionally, if the evoked potential waveform 706 is not detected by the sensing circuitry 158, the clinician may adjust a position of the lead (e.g., the lead 310, the leads 410, 412) during the intraoperative placement procedure. For example, the controller 151 may determine that when no evoked potential waveform 706 is detected (e.g., the morphology of the evoked potential waveform 706 does not include any peaks or remains below a threshold) and/or measured by the sensing circuitry 158, the excitation pulses 506 are not stimulating neurons of the select dermatome. The IPG 350 may transmit a message to the external device 160 informing the clinician to adjust a position of the corresponding lead emitting the excitation pulses 506 (e.g., the first lead 410, the second lead 412).

Optionally, the sensing circuitry 158 may measure the evoked potentials resulting from the excitation pulses 506 at one or more of the electrodes 303 of the lead 412. Additionally or alternatively, the sensing circuitry 158 may measure the evoked potentials at additional leads coupled to the IPG 350 positioned at an alternative DR or DRG.

During intraoperative targeting of the lead (e.g., the lead 310, the lead 412) the IPG 350 may compare the evoked potentials measured by the sensing circuitry 158 to determine which dermatomes are being stimulated by the excitation pulses 506. Multiple leads positioned at corresponding dermatomes may allow the IPG 350 to distinguish between the dermatomes affected by the excitation pulses 506 while the patient is kept under general anesthesia. For example, the IPG 350 may be electrically coupled to the lead 410, 412 and a third lead. The third lead may include one or more electrodes proximate to a second DR corresponding to a second dermatome (e.g., a higher or lower dermatome) different than the select dermatome corresponding to the DR 308. The IPG 350 may determine that evoked potentials detected from the third lead corresponds to stimulation of the second dermatome and evoked potentials detected from the lead 412 corresponds to stimulation of the select dermatome.

At 210, determine from a morphology of the evoked potential waveform 706 activation of one or more sensory fiber types. The morphology may correspond to a peak amplitude, a number of peaks, peak width, peak latency, descending and/or ascending slopes, and/or the like of the evoked potential waveform 706. The morphology of the evoked potential waveform 706 may be determined by the controller 151 and/or the sensing circuitry 158, for example, based on changes in subsequent electrical potential measurements.

For example, the sensing circuitry 158 acquired a plurality of electrical potential measurements (e.g., 708, 714) over time at the electrode 303a. The plurality of electrical potential measurements form the evoked potential waveform 706. The electrical measurement 708 having a voltage value 712 was acquired at 710, and the electrical measurement 714 having a voltage value 718 was acquired at 716. The electrical measurement 714 was measured by the sensor circuitry 158 subsequent to the electrical measurement 708. The controller 151 may compare the time 710, 716 and voltage values 712 and 718 of the electrical measurements 708 and 714, respectively, to determine a slope of the evoked potential waveform 706 between the electrical measurements 708 and 714. The slope represents a ratio of the change in voltage values 712, 718 and the change in time 710, 716.

The controller 151 may continually determine additional slopes for the evoked potential waveform 706 between adjacent electrical measurements (e.g., the electrical measurements 714 and 720, the electrical measurements 720 and 722, the electrical measurements 722 and 724) during a predetermined time period 740. The predetermined time period 740 may be a value stored on the memory 161 corresponding to an amount of time the sensing circuitry 158 acquires electrical measurements at the electrode 303a.

Optionally, the predetermined time period 740 may depend on when the excitation pulses 506 are emitted from the first electrode (e.g., the electrode 302a of FIG. 3). For example, the start of the predetermined time period 740 may be based on when the electrode 302a emits the excitation pulses 506 to the stimulation target.

Based on changes in the magnitude and/or direction of the slopes the controller 151 may determine a number of peaks of the evoked potential waveform 706 with a corresponding amplitude (e.g., 750-754). For example, the controller 151 may determine a slope of the evoked potential waveform 706 between the electrical measurements 720 and 722 is negative, and a slope of the evoked potential waveform 706 between the electrical measurements 722 and 724 is positive. Based on the change in magnitude of the slope from negative to positive, the controller 151 may determine that a peak, particularly a negative peak 726, occurs between the electrical measurements 720 and 724.

An amplitude (e.g., 750-754) of the peak may correspond to the extent of activation of different types of sensory fibers (e.g., the A$\beta$ sensory, A$\delta$ sensory, and/or C sensory fibers). For example, a patient may feel more paresthesia from excitation pulses that result in an evoked potential generated by the A$\beta$ sensory fiber with a high amplitude relative to excitation pulses that result in an evoked potential with a lower amplitude. The amplitudes 750-754 may be determined by the controller 151 based on a peak value (e.g., apex, vertex of intersections of adjacent slopes) of the negative peaks 726-730 with respect to a baseline 760 (e.g., common ground of the NS system 100). The amplitudes 750-754 may be stored by the controller 151 on the memory 161. Optionally, the amplitudes 750-754 may be transmitted to the external device 160 by the communication circuitry 155.

It should be noted that in other embodiments, the negative peaks 726-730 and/or the evoked potential waveform 706 may have an opposite polarity than shown in FIG. 7. For example, the evoked potential waveform 706 may have positive peaks.

The evoked potentials are generated by a population of neurons of one or more sensory fiber types proximate to the stimulation target. The evoked potentials travel away from the stimulation target towards the first and second series of electrodes 302 and 303. A latency of the evoked potentials is based on an action potential propagation speed of the sensory fiber type, which corresponds to the fiber size and myelination of the fiber. For example, the A$\beta$ sensory fiber is larger than the A$\delta$ sensory fiber and the C sensory fiber. Thus, an evoked potential generated by the A$\beta$ sensory fiber may travel faster relative to an evoked potential generated by the A$\delta$ sensory fiber and/or unmyelinated C sensory fiber.

In another example, the A$\delta$ sensory fiber is larger than the C sensory fiber. Thus, an evoked potential generated by the A$\delta$ sensory fiber may travel faster relative to an evoked potential generated by the C sensory fiber.

Figure 8:
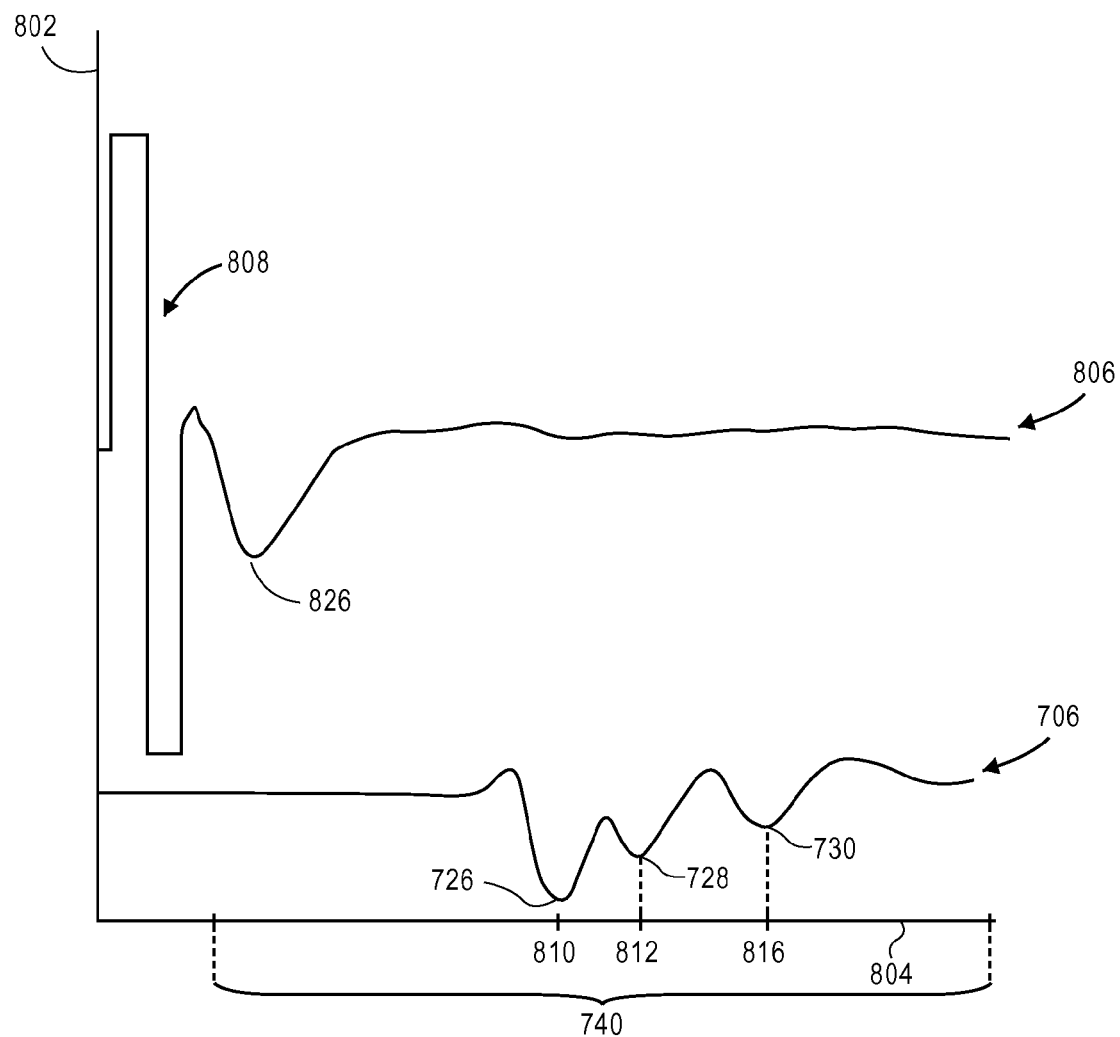
FIG. 8 illustrates graphical representations of electrical potential measurements at a first and second electrode, in accordance with an embodiment.

In connection with FIG. 8, when the evoked potentials generated by the sensory fibers travel further from the stimulation target, the peaks of the evoked potentials corresponding to each sensory fiber further separate with respect to each other in time. The separation or latency of the evoked potentials with respect to each other may be used by the controller 151 to distinguish between the evoked potentials generated by the sensory fibers corresponding to activation of the sensory fibers.

FIG. 8 illustrates graphical representations of electrical potential measurements at the electrode 302a and 303a. A horizontal axis 804 represents time, and a vertical axis 802 represents a voltage of sensed electrical potentials measured at the electrode 303a. The electrical potential measurements form an evoked potential waveform 806, which is measured by the sensing circuitry 158 at the electrode 302a resulting from the excitation pulses.

For example, the electrode 302a emits excitation pulses received from the IPG 350 towards neurons corresponding to the stimulation target (e.g., one or more dermatomes) within the DC 306. The evoked potential waveform 806 includes a stimulation induced artifact component 808. The component 808 is an electrical artifact in the electrical measurements of the evoked potential waveform 806 due to the excitation pulses 506 emitted by the electrode 302a. Optionally, the controller 151 and/or sensing circuitry 158 may filter out the component 808 by automatically adjusting the gain concurrently when the excitation pulses 506 are delivered to the electrode 302a or blanking the sensing amplifiers of the sensing circuitry 158 by connecting the amplifiers to ground during stimulation.

The excitation pulses 506 may generate evoked potentials within the neurons. The evoked potentials travel along the afferent nerve fibers of the Aβ sensory fiber, the Aδ sensory fiber, and the C sensory fiber during subsequent orthodromic and antidromic propagation towards the electrode 302a and 303a. The evoked potentials may adjust and/or change the electrical potential at and/or proximate to the electrodes 302a and 303a. Due to the proximity of the electrode 302a to the stimulated target, for example the DC 306, the evoked potentials may be measured at the electrode 302a before the electrode 303a.

The sensing circuitry 158, electrically coupled to the electrode 302a, may measure and/or detect the evoked potentials corresponding to the change in electrical potential over time at the electrodes 302a at the sampling and/or acquisition frequency. The evoked potential waveform 806 includes a negative peak 826 corresponding to the activation of one or more sensory fibers. The negative peak 826 may include multiple evoked potentials generated by the sensor fibers. For example, the negative peak 826 may include an amplitude corresponding to evoked potential generated by the Aβ sensory fiber, the Aδ sensory fiber, and/or C sensory fiber.

The evoked potentials travel along the corresponding sensory fibers at different rates based on the action potential propagation speed of the sensory fiber towards the electrode 303a, forming the evoked potential waveform 706. The different rates of antidromic propagation of the evoked potentials traversing along the sensory fibers may result in differences in latency of the evoked potentials arriving at the electrodes 303. The latency of the evoked potentials are illustrated by three negative peaks 726-730 of the evoked potential waveform 706 that correspond to activation of the sensory fibers. The controller 151 may assign a sensory fiber corresponding to each negative peak 726-730 based on the peak latency or when the negative peak 726-730 is measured and/or detected by the sensing circuitry 158 at the electrode 303a.

For example, the controller 151 may use the peak latencies of the evoked potential waveform 706, based on the peak latencies of the negative peaks 726-730, to distinguish between the different sensory fiber types. The negative peak 726 is measured by the sensing circuitry 158 at 810, which is before the negative peaks 728-730. The controller 151 may determine since the negative peak 726 was measured prior to the remaining negative peaks 728-730 during the predetermined time interval 740 the negative peak 726 corresponds to the Aβ sensory fiber. The negative peak 728, measured at 812 and positioned between the negative peaks 726 and 730 may be determined by the controller 151 to correspond to the Aδ sensory fiber. The controller 151 may determine that the negative peak 730 measured at 816 and subsequent to the negative peaks 726-728 corresponds to the C sensory fiber.

It should be noted that the electrical potential measurements, measured at the electrodes 303 may have a higher fidelity than the electrical potential measurements measured at the electrodes 302. For example, the intradural space between the DR 308, which contains the sensory fibers, and the electrodes 303 is smaller than the intradural space between the DC 306 and the lead 410 and/or the portion 312 position. The intradural space further has less cerebral spinal fluid between the electrodes 303 and the DR 308 relative to the intradural space separating the electrodes 302 from the DC 306. The cerebral spinal fluid may affect the electrical characteristics of the evoked potentials generated by the sensory fibers prior to being measured by the electrodes 302, 303. For example, the electrical currents generated by the evoked potentials may be dispersed within the cerebral spinal fluid and reduce the electrical potential of the evoked potential. By positioning the electrodes 303 closer to the sensory fibers, the effect of the cerebral spinal fluid on the electrical potential measurements of the evoked potentials are reduced relative to the electrodes 302; increasing the fidelity of the electrical potential measurements measured at the electrodes 303 relative to the electrical potential measurements measured at the electrodes 302.

Additionally, when the patient changes position, the lead 410 or the portion 312 of the lead 310 may move and/or change position relative to the DC 306. Changes in position of the electrodes 302 may alter which dermatome and/or combination of dermatomes the electrical potential measurements correspond to, reducing the fidelity of the electrical potential measurements acquired at the electrodes 302. The position of electrodes 303 near the DR is not as affected by patient changes in position relative to the position of the lead 410 or the portion of the lead 310, reducing the effects of changing a posture of the patient on the electrical potential measurements of the electrodes 303. For example, during changes in patient posture the electrodes 303 may have negligible to relatively little motion compared to the electrodes 302 increasing the fidelity of the electrical potential measurements at the electrodes 303 relative to the electrical potential measurements at the electrode 302.

At 212, adjust the stimulation level based on the morphology of the evoked potential waveform 706. The activation of the Aβ sensory fiber is associated with paresthesia and non-painful information. Conversely, the activation of the Aδ sensory fiber and/or the C sensory fiber is associated with painful stimuli. The controller 151 may adjust the stimulation level to increase the activation of the Aβ sensory fiber and/or to decrease the activation of the Aδ sensory fiber and/or the C sensory fiber.

For example, the controller 151 may adjust at least one of an amplitude, polarity, pulse width, or frequency corresponding to the stimulation level of the excitation pulses 506 delivered by the IPG 150. Additionally or alternatively, the controller 151 may select a different electrode 302 and/or additional electrodes 302 for emitting the excitation pulses 506. Optionally, the controller 151 may receive a new stimulation level and/or adjust the stimulation level based on instructions received by the external device 160. For example, the external device 160 may instruct the controller 151 to adjust the stimulation level by changing the pattern of the excitation pulses 506 from a tonic stimulation waveform to a burst stimulation waveform.

The morphology of the evoked potential may be altered due to changes in patient posture or migration of the stimulation or recording leads. Changes in evoked potential morphology can be used to detect a variation in patient posture or lead location, and adjust stimulation parameters accordingly.

Figure 9A:
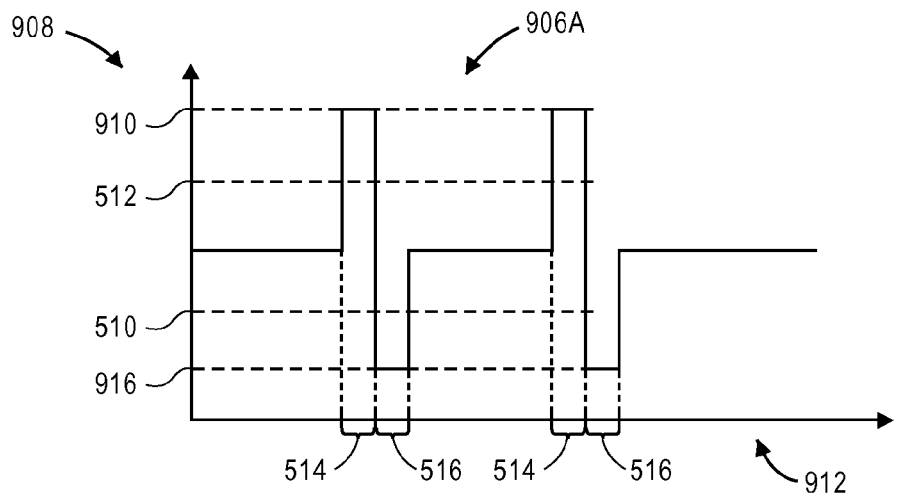
FIG. 9*a* is a graphical representation of excitation pulses having an increased amplitude relative to the excitation pulses in FIG. 5.
Figure 9B:
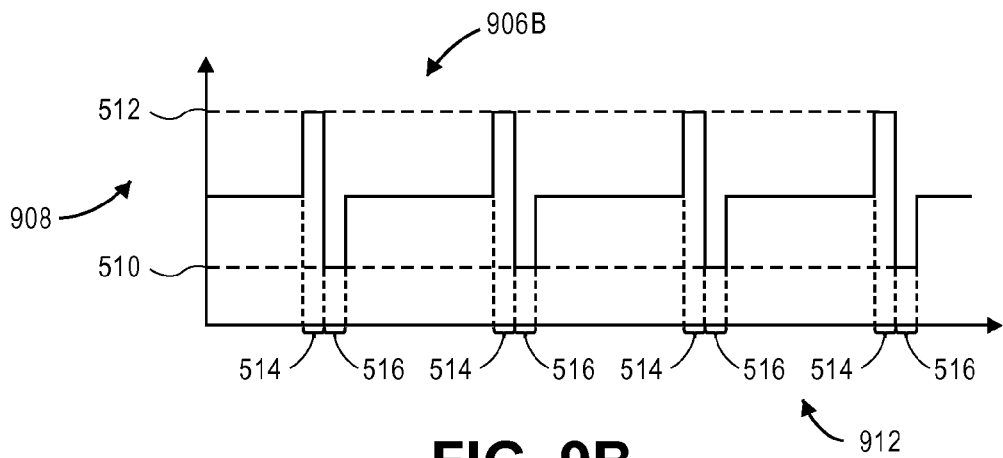
FIG. 9*b* is a graphical representation of excitation pulses having an increased frequency relative to the excitation pulse in FIG. 5.
Figure 9C:
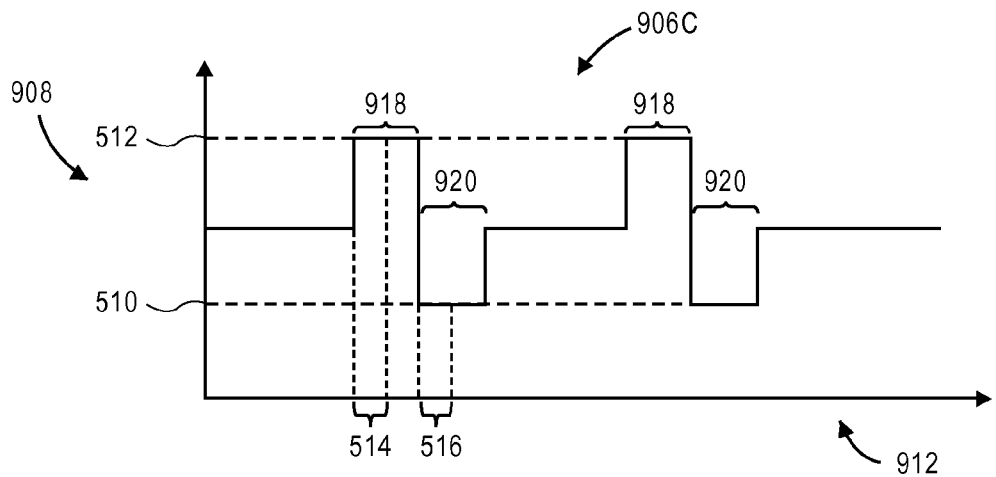
FIG. 9*c* is a graphical representation of excitation pulses having an increased pulse width relative to the spinal cord stimulation pulses in FIG. 5.

FIGS. 9a-c are graphical representations of exemplary excitation pulses 906a-c with an adjusted stimulation level relative to the excitation pulses 506 of FIG. 5. A horizontal axis 912 represents time, and a vertical axis 908 may represent voltage or an electrical potential. It should be noted that the stimulation level may be adjusted in additional or alternative ways to what is shown in FIGS. 9a-c. For example, adjusting the polarity of the excitation pulses 506.

FIG. 9a illustrates SCS pulses 906a having an increased amplitude 910 and 916 over the amplitudes 514 and 516 of the excitation pulses 506. It should be noted that in other embodiments the duration 514, the duration 516 and/or the number of the excitation pulses 906a may be increased as well. It should be noted that although the amplitudes 910 and 916 are shown being increased in equal magnitude, alternative embodiments may not. For example, the positive amplitude 910 may have a greater amplitude than the negative amplitude 916.

FIG. 9b illustrates excitation pulses 906b having an increased number of excitation pulses 906b relative to the excitation pulses 506 over the same time period. For example, the excitation pulses 906b may have a higher frequency relative to the excitation pulses 506. It should be noted that in other embodiments the duration 514, the duration 516, the amplitude 510 and/or the amplitude 512 of the excitation pulses 906b may be increased as well.

FIG. 9c illustrates excitation pulses 906c having an increased duration 918 and 920 (e.g., pulse width) relative to the duration 514 and 516 of the excitation pulses 506. It should be noted that in other embodiments the amplitude 510 and 512 and/or number of the excitation pulses 906c may be increased as well. It should be noted that although the durations 918 and 920 are shown being increased in equal magnitude, in alternative embodiments the duration 918 and 920 may not have an equal magnitude. For example, the duration 918 may be longer than the duration 920.

Figure 10:
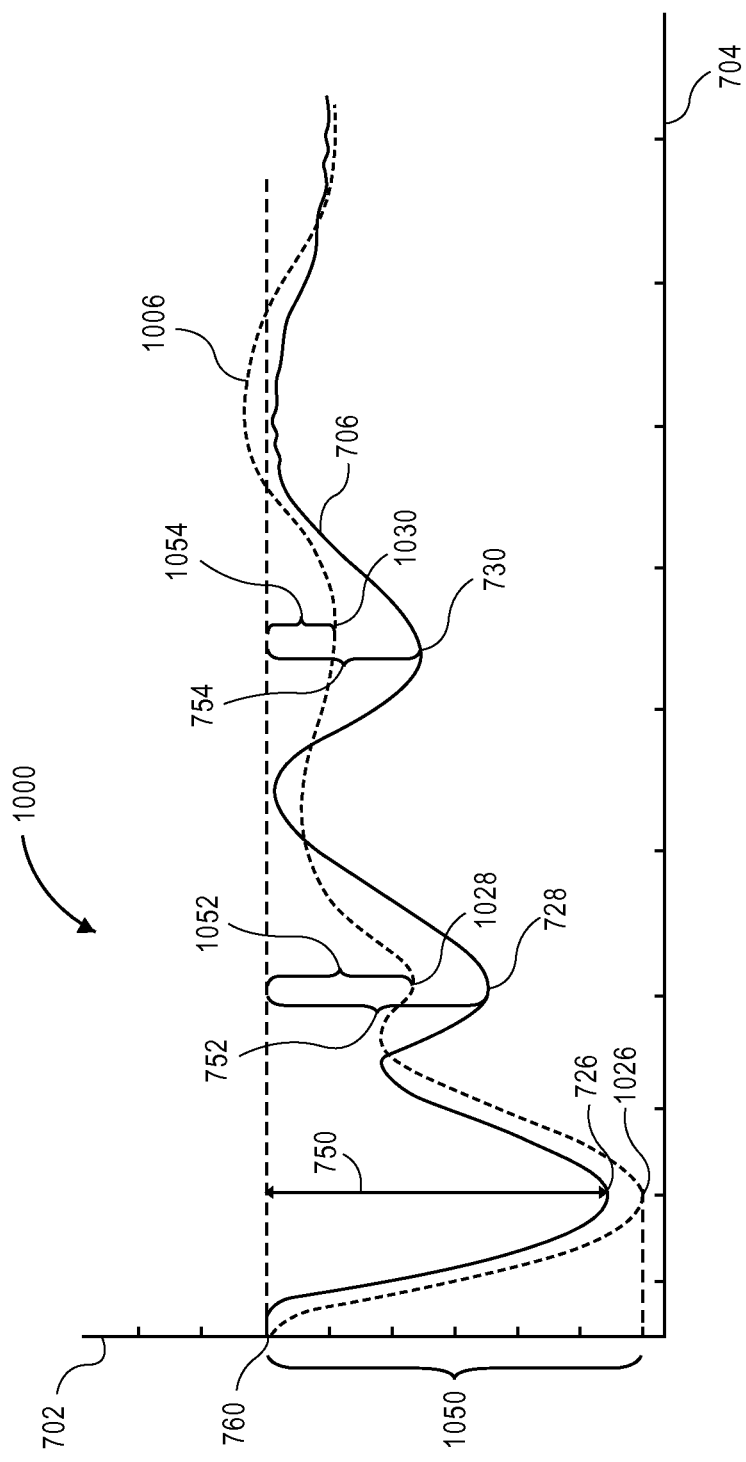
FIG. 10 illustrates a graphical representation of evoked potential waveforms, in accordance with an embodiment.

FIG. 10 illustrates a graphical illustration 1000 of the evoked potential waveform 706 and an evoked potential waveform 1006 resulting from adjustments to the stimulation level. The controller 151 may determine from the morphology (e.g., peak amplitude, ascending and/or descending slope, number of peaks) negative peaks 1026-1030 of the evoked potential waveform 1006 corresponding to activation of the Aβ sensory fiber, the Aδ sensory fiber, and the C sensory fiber, for example as described at 210. The amplitudes 1050-1054 of the negative peaks 1026-1030 may be changed relative to the amplitudes 750-754 of the evoked potential waveform 706 based on the adjusted stimulation level.

The controller 151 may compare the amplitudes 1050-1054 with the amplitudes 750-754 to determine whether to further adjust the stimulation level. For example, the controller 151 may adjust the stimulation level to reduce the amplitudes 1052-1054 corresponding to the Aδ sensory fiber, and the C sensory fiber.

Additionally or alternatively, the lead (e.g., the lead 310, the lead 410, the lead 412) may be repositioned based on the morphology of the evoked potential waveform. For example, if the evoked potential waveform does not include any peaks and/or remains below an activation threshold the controller 151 may determine that the one or more electrodes (e.g., 302, 303) delivering the excitation pulses 506 has shifted and no longer stimulates the stimulation target.

Figure 11:
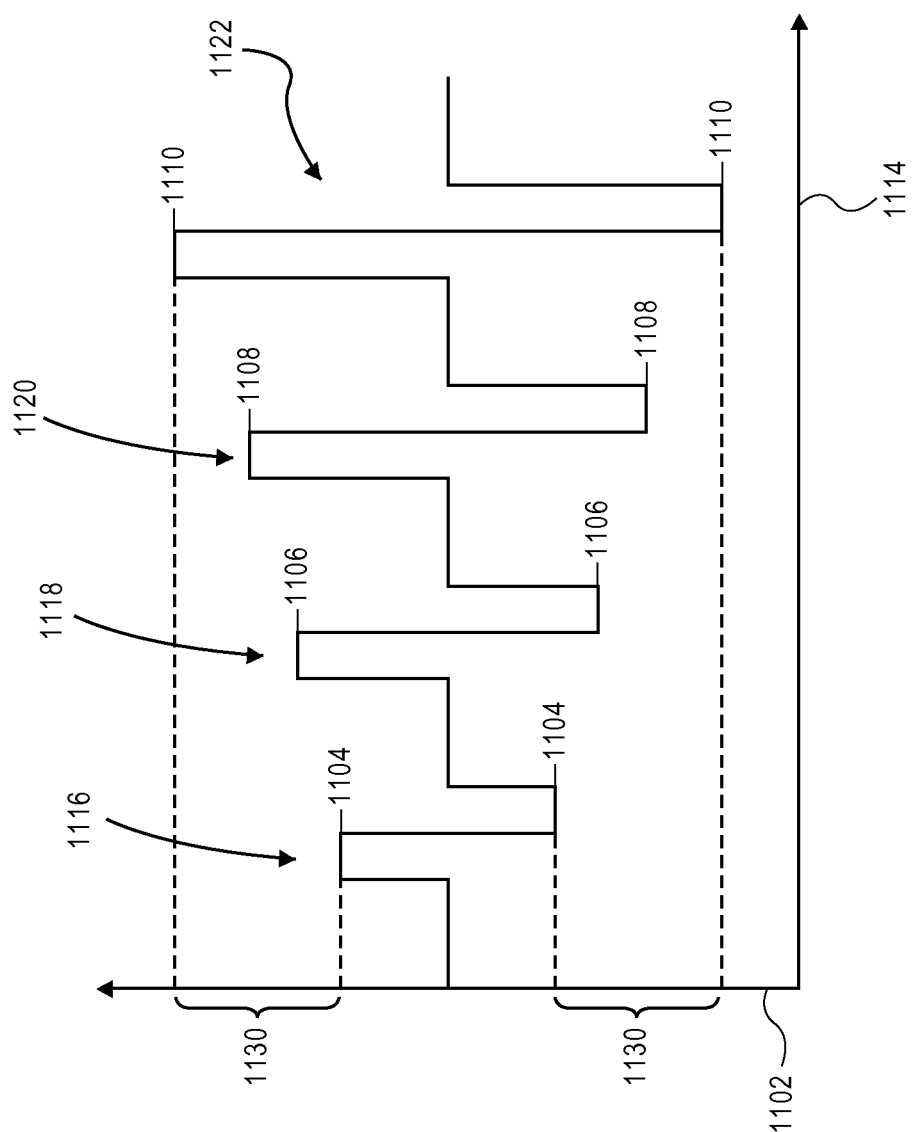
FIG. 11 is a graphical representation of a series of excitation pulses according to a testing procedure, according to an embodiment of the present disclosure.
Figure 12:
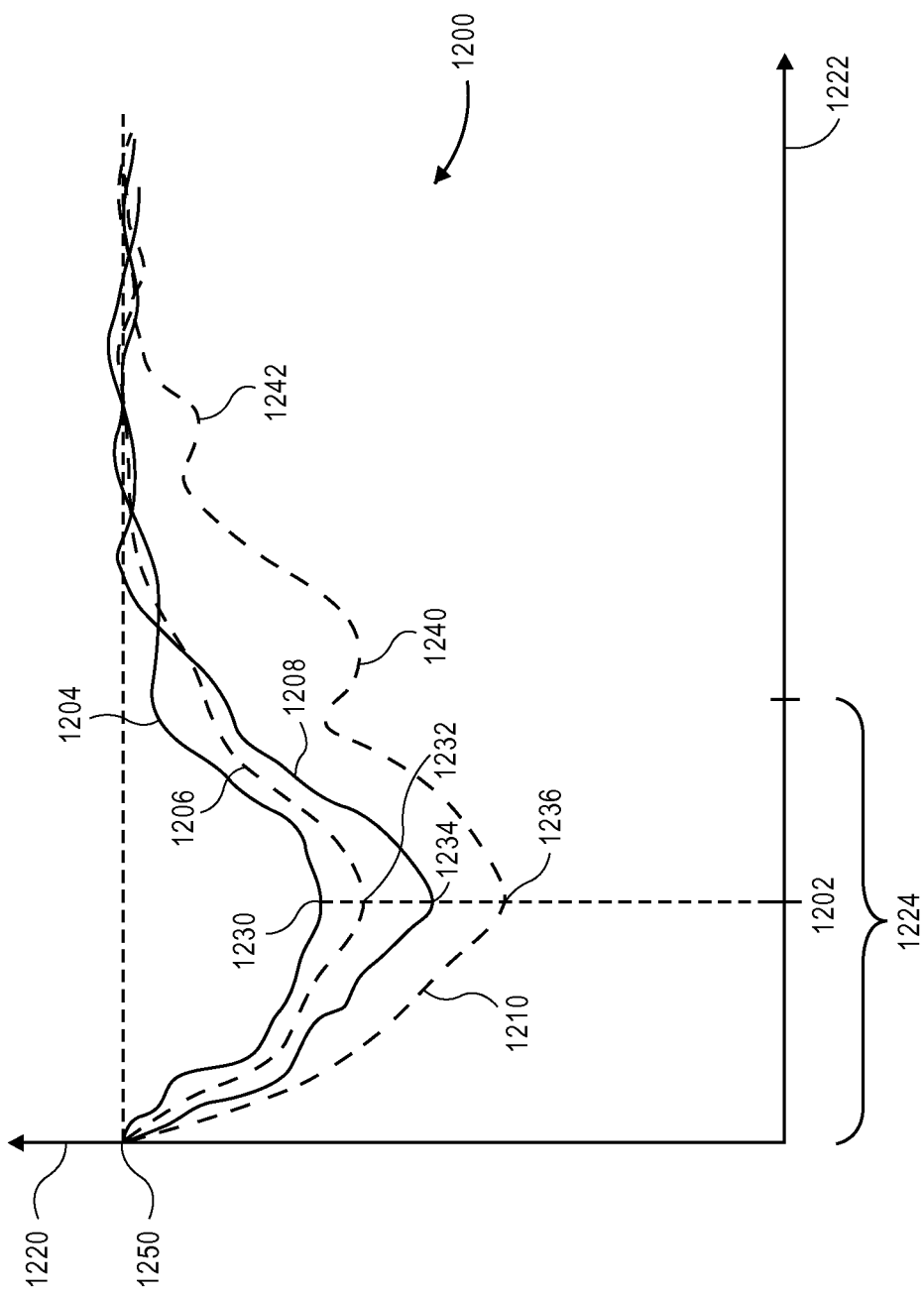
FIG. 12 is a graphical representation of evoked potential waveforms, according to an embodiment of the present disclosure.
Figure 13:
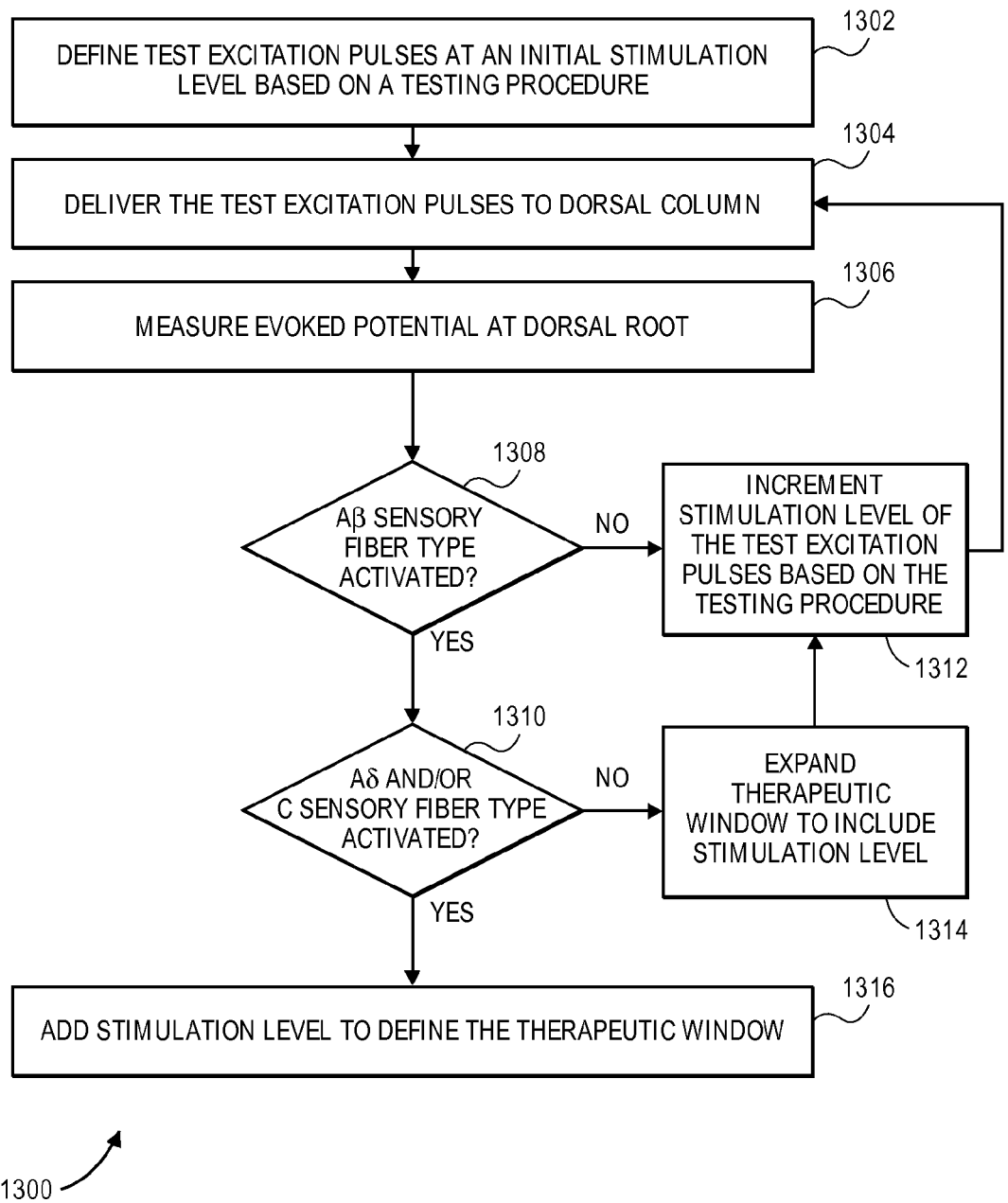
FIG. 13 is a flowchart of a method for defining a therapeutic window, in accordance with an embodiment.

In connection with FIGS. 11-13, optionally, the controller 151 may adjust the stimulation level to an adjusted stimulation level based on a testing procedure to determine a therapeutic window 1130 shown in FIG. 11. The therapeutic window 1130 may correspond to a range of stimulation parameters (e.g., amplitude, frequency, pulse width) of test excitation pulses 1116-1122 based on activation of the Aβ sensory fiber, the Aδ sensory fiber, and/or the C sensory fiber determined by the controller 151 from evoked potential recordings. For example, the therapeutic window 1130 may correspond to a maximum amplitude that can be applied by the electrodes 302 without activating the Aδ sensory fiber and/or the C sensory fiber that are associated with pain. Additionally or alternatively, the range of stimulation parameters within the therapeutic window 1130 may result in activation of the Aβ sensory fiber and/or minimal or lower activation of the Aδ sensory fiber and/or the C sensory fiber relative to other stimulation levels or parameters of excitation pulses outside the therapeutic window 1130.

FIG. 13 is a flowchart of a method 1300 for determining the therapeutic window. The method 1300 may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It should be noted, other methods may be used, in accordance with embodiments herein.

One or more methods may (i) adjust a stimulation level based on a testing procedure, and (ii) iteratively repeat the measuring (e.g., the method 200 at 208), determining (e.g., the method 200 at 210), and adjusting (e.g., the method 200 at 212) operations of the method 200 until a therapeutic window is defined.

Beginning at 1302, test excitation pulses 1116 are defined at an initial stimulation level based on a testing procedure. The testing procedure may be stored on the memory 161 and/or received by the external device 160. The testing procedure may include algorithms and/or adjustment parameters for initial test excitation pulses 1116 as well as for adjusting test excitation pulses 1116-1122 to determine the therapeutic window 1130 as described in the method 1300. Optionally, the testing procedure may be based on the SCS program to determine the stimulation levels for the excitation pulses for SCS. In connection with FIG. 11, the testing procedure may generate a series of test excitation pulses 1116-1120, such that each subsequent test excitation pulse generates a different evoked potential waveform 1204-1210. For example, the testing procedure may increment the stimulation level of the test excitation pulses to activate one or more of the sensory fibers.

FIG. 11 illustrates the series of test excitation pulses 1116-1122 delivered by the IPG 350 and emitted by at least one of the electrodes 302 of FIG. 3. A horizontal axis 1114 may represent time, and a vertical axis 1102 may represent voltage or electrical potential. The test excitation pulses 1116 may correspond to an initial stimulation level having an amplitude of 1104.

At 1304, the test excitation pulses 1116 are delivered to the DC 306. For example, the IPG 350 may deliver the test excitation pulses 1116 to one or more of the electrodes 302 similar to and/or the same as the deliver operation at 204. It should be noted that although the test excitation pulses 1116-1122 are shown having a tonic or biphasic waveform, in other embodiments the one or more excitation pulses 1116-1122 may be a burst waveform, or the like.

Additionally or alternatively, the test excitation pulses 1116 may be delivered to the DR 308, the DRG 602 (FIG. 6), or the spinal nerve 606. For example, the IPG 350 may deliver the test excitation pulses 1116 to one or more of the electrodes 303.

At 1306, one or more of the evoked potential waveforms 1204-1210 are measured at the DR. FIG. 12 is a graphical representation 1200 of evoked potential waveforms 1204-1210 generated by the Aβ sensory fiber, the Aδ sensory fiber, and/or the C sensory fiber in response to the test excitation pulses 1116-1122. A horizontal axis 1222 represents time, and a vertical axis 1220 may represent voltage or electrical potential. The evoked potential waveform 1204 corresponds to the excitation pulses 1116, the evoked potential waveform 1206 corresponds to the excitation pulses 1118, the evoked potential waveform 1208 corresponds to the excitation pulses 1120, and the evoked potential waveform 1210 corresponds to the excitation pulses 1122. The evoked potential waveforms 1204-1210 are shown aligned at negative peaks 1230-1236 of the evoked potential waveforms 1204-1210. The evoked potential waveforms 1204-1210 may be measured by the sensing circuitry 158 at one or more electrodes 303 proximate to the DR 308, for example, as described at 208 of FIG. 2.

At 1308, determine whether the Aβ sensory fiber is activated. For example, the controller 151 may determine activation of the Aβ sensory fiber based on the morphology of the measured evoked potential waveform 1204-1210 as described at 210. For example, the controller 151 may determine slopes of the evoked potential waveform 1204 between electrical potential measurements. The controller 151 may identify a negative peak 1230 based on the direction of the slopes, such as ascending, descending, and/or approximately zero or flat. For example, the controller 151 may identify a location of the negative peak 1230 based on adjacent descending and ascending slopes.

Optionally, the controller 151 may compare the magnitude of the slopes with a predetermined value to determine whether the direction of the slope is ascending, descending, and/or approximately zero or flat. For example, a magnitude of the slope below the predetermined value may be determined by the controller 151 to be approximately flat. Reducing the chances of the controller 151 determining false negative peaks from slight and/or minimal changes in electrical potential measurements due to noise, interference, and/or the like.

Additionally or alternatively, the controller 151 may determine an amplitude of the negative peak 1230 by comparing a peak value (e.g., apex, a vertex or intersection of adjacent slopes of the negative peak 1230 with respect to a baseline 1250 (e.g., common ground of the NS system 100). The controller 151 may compare the amplitude with a predetermined value to determine whether the change in magnitude of adjacent slopes correspond to a negative peak. For example, when the amplitude is below the predetermined value the controller 151 may determine that adjacent slopes having contrasting magnitudes do not form a negative peak. In another example, when the amplitude is above the predetermined value the controller 151 may determine that the adjacent slopes correspond to a negative peak.

Based on a location of the negative peak 1230, the controller 151 may determine whether the negative peak 1230 corresponds to activation of an Aβ sensory fiber. For example, since the Aβ sensory fiber is more conductive than the alternative sensory fibers, such as the Aδ sensory fiber and/or the C sensory fiber, the Aβ sensory fiber may be detected by the sensing circuitry 158 before a negative peak corresponding to activation of the alternative sensory fibers. Additionally or alternatively, the controller 151 may determine that a negative peak occurring within a predetermined time 1224, such as 1 ms, after the delivery of the test excitation pulses 1116 corresponds to the Aβ sensory fiber.

If the Aβ sensory fiber is not activated, then at 1312, increment the stimulation level of the test excitation pulses 1116 at a constant rate based on the testing procedure. The testing procedure may instruct the controller 151 to increment the stimulation level by increasing at least one of the amplitude 1104, the pulse width, and/or the frequency of the test excitation pulses 1116 at the constant rate (e.g., 1%, 2%, 5%, 10%) to form subsequent test excitation pulses, such as the test excitation pulses 1118. Additionally or alternatively, the testing procedure may adjust the rate incremented by the controller 151 based on the stimulation level. For example, the testing procedure may increase the stimulation level at a higher rate for stimulation levels below a threshold relative to stimulation levels above the threshold.

Optionally, the testing procedure may implement a pseudo random adjustment pattern. For example, the testing procedure may increment the stimulation level based on a pseudo random adjustment corresponding to at least one of the amplitude 1104, the pulse width, and/or the frequency of the test excitation pulses 1116 to generate subsequent test excitation pulses 1118-1122. The increment may be pseudo random such that adjustments to the stimulation level between adjacent excitation pulses 1116-1122 may be different relative to previous and/or subsequent adjustments to excitation pulses 1116-1122.

Additionally or alternatively, the lead (e.g., the lead 310, the lead 410, the lead 412) may be repositioned based on the morphology of the evoked potential waveform. For example, if the measured evoked potential does not include any peaks and/or remains below an activation threshold the controller 151 may determine that the one or more electrodes (e.g., 302, 303) delivering the excitation pulses 1116 has shifted and no longer stimulates the stimulation target.

If the Aβ sensory fiber is activated, then at 1310, determine whether the Aδ sensory fiber and/or the C sensory fiber is activated. The controller 151 may determine activation of the Aδ sensory fiber and/or the C sensory fiber based on the morphology of the measured evoked potential waveform 1204-1210 as described at 210 of FIG. 2. For example, the controller 151 may determine slopes of the evoked potential waveform 1210 between electrical potential measurements or evoked potential recordings. The controller 151 may identify negative peaks 1240 and 1242 based on the direction of the slopes, such as ascending, descending, and/or zero.

Based on a location of the negative peaks 1240, 1242, the controller 151 may determine whether the negative peaks 1240, 1242 correspond to activation of the Aδ sensory fiber and/or the C sensory fiber. For example, since the Aβ sensory fiber has a faster action potential propagation speed than the Aδ sensory fiber and/or the C sensory fiber, evoked potentials generated by the Aδ sensory fiber and/or the C sensory fiber may be detected by the sensing circuitry 158 after the negative peak 1236 corresponding to activation of the Aβ sensory fiber. For example, the controller 151 may determine that since the negative peak 1240 occurs after the negative peak 1236, the negative peak 1240 corresponds to activation of the Aδ sensory fiber. Additionally or alternatively, the controller 151 may determine that a negative peak occurring outside a predetermined time 1224, such as 1 ms, after the delivery of the test excitation pulses 1116-1122 corresponds to the Aδ sensory fiber and/or the C sensory fiber.

Additionally or alternatively, the controller 151 may determine an amplitude of one or more of the negative peaks 1240, 1242 by comparing peak values (e.g., apex, vertex of intersections of adjacent slopes) of the negative peaks 1240, 1242 with respect to a baseline 1250 (e.g., common ground of the NS system 100). The controller 151 may compare one or both of the amplitudes with a predetermined value to determine whether the change in magnitude of adjacent slopes correspond to a negative peak and/or the pain attributed to activation of the Aδ sensory fiber and/or the C sensory fiber is present. For example, when the amplitude of the negative peaks are below the predetermined value the controller 151 may determine that the Aδ sensory fiber and/or the C sensory fiber is not activated. In another example, when the amplitude of the negative peaks are above the predetermined value the controller 151 may determine that the Aδ sensory fiber and/or the C sensory fiber is activated.

If the Aδ sensory fiber and/or the C sensory fiber is not activated, then at 1314, the controller 151 may expand the therapeutic window 1130 to include the stimulation level. For example, the controller 151 may determine that the evoked potential waveform 1210 does not include negative peaks corresponding to activation of the Aδ sensory fiber and/or the C sensory fiber. The controller 151 may include the one or more parameters, such as the amplitude 1108, pulse width, and/or the like corresponding to the stimulation level of the test excitation pulses 1120 resulting in the evoked potential waveform 1210 to the therapeutic window 1130 stored on the memory 161.

In another example, the controller 151 may determine that the negative peaks 1240 and 1242 corresponding to evoked potentials generated by the Aδ sensory fiber and/or the C sensory fiber have amplitudes that are below the predetermined value. The controller 151 may include the one or more parameters, such as the amplitude 1110, pulse width and/or the like corresponding to the stimulation level of the test excitation pulses 1122 to the therapeutic window 1130 stored on the memory 161.

If the Aδ sensory fiber and/or the C sensory fiber is activated, then at 1316 the controller 151 may add the stimulation level to define the therapeutic window 1130. The controller 151 may define the therapeutic window 1130 from the range of stimulation parameters based on the initial stimulation level to the stimulation level resulting in activation of the Aδ sensory fiber and/or the C sensory fiber. For example, the controller 151 may define the therapeutic window 1130 from the amplitude 1104 of the initial stimulation level of the test excitation pulses 1116 to the amplitude 1110 of the stimulation level of the test excitation pulses 1122.

Additionally or alternatively, if the Aδ sensory fiber and/or the C sensor is activated at 1310 the controller 151 may reduce the stimulation level to determine a maximum stimulation level resulting in minimal or no activation of the Aδ sensory fiber and/or the C sensory fiber relative to the stimulation level resulting in activation of the Aδ sensory fiber and/or the C sensory fiber determined at 1310. For example, the controller 151 may determine that the test excitation pulses 1122 result in activation of the Aδ sensory fiber and/or the C sensory fiber. The controller 151 may reduce one or more stimulation parameters (e.g., the amplitude 1110, pulse width) corresponding to the stimulation level of the test excitation pulses 1122.

For example, the controller 151 may reduce the stimulation level at a point between the stimulation level of the test excitation pulses 1120 and 1122. And the controller 151 may iteratively adjust between one or more stimulation parameters that correspond to a stimulation level between the stimulation levels of the test excitation pulses 1120 and 1122 to determine a stimulation level having a maximum stimulation parameter (e.g., amplitude, pulse width) that is above the test excitation pulses 1120 and below the test excitation pulses 1122 that does not result in activation of the Aδ sensory fiber and/or the C sensory fiber.

Optionally, the therapeutic window 1130 may be based on one or more stimulation levels that result in an amplitude (e.g., 750, 1050) corresponding to activation of the Aβ sensory fiber greater than a predetermined baseline. Additionally or alternatively, the therapeutic window 1130 may be based on one or more stimulation levels that result in an amplitude (e.g., 752-754, 1052-1054) corresponding to activation of the Aδ sensory fiber and/or the C sensory fiber less than a predetermined threshold.

Optionally, the controller 151 may adjust the stimulation level based on the morphology of an evoked potential waveform measured at one or more electrodes of a third lead coupled to the IPG 350. For example, the IPG 350 may be coupled to the lead 410, 412 and a third lead. The third lead may include one or more electrodes proximate to a second DR corresponding to a second dermatome (e.g., a higher or lower dermatome) different than the select dermatome corresponding to the DR 308. Additionally or alternatively, the third lead may be positioned at a contralateral DR corresponding to the DR 308 (e.g., a contralateral side with respect to the DR 308). The sensing circuitry 158 may measure the evoked potential waveform from the one or more electrodes of the third lead resulting from the excitation pulses 506. Based on the evoked potential recordings from the one or more electrodes of the third lead, the controller 151 may adjust the stimulation level of the excitation pulses 506.

For example, the third lead is positioned proximate to a second DR corresponding to a second dermatome not intended to be stimulated based on the SCS program. The controller 151 may determine activation of a sensory fiber of the second dermatome based on electrical potential measurements measured at one or more electrodes of the third lead. For example, the controller 151 may determine activation of the sensory fiber, such as the Aβ sensory fiber, based on a morphology (e.g., negative peak) of an evoked potential waveform formed from the electrical potential measurements as described at 210 of FIG. 2.

The controller 151 may adjust or tune the excitation pulses 506. In various embodiments, the controller 151 may adjust the excitation pulses 506 to maximize an amplitude (e.g., the amplitude 750 of FIG. 7) of a negative peak (e.g., the negative peak 726) of an evoked potential waveform corresponding to an activation of a sensory fiber of the select dermatome and/or to minimize the amplitude of a negative peak of the evoked potential waveform corresponding to activation of a sensory fiber of the second dermatome. For example, the controller 151 may adjust the stimulation level of the excitation pulses 506 and/or select additional and/or alternative electrodes 302 to emit the excitation pulses 506. The adjustments to the excitation pulses 506 by the controller 151 may redirect the stimulation of the excitation pulses 506 away from the second dermatome and/or toward the select dermatome within the DC 306.

For example, the adjusted stimulation level of the excitation pulses 506 may reduce an amplitude of a negative peak (e.g., 726) of the evoked potential waveform measured at the one or more electrodes of the third lead corresponding to activation of the sensory fiber of the second dermatome. Additionally, the adjusted stimulation level of the excitation pulses 506 may increase an amplitude of a negative peak (e.g., 726) of the evoked potential waveform generated by a sensory fiber of the select dermatome. Additionally or alternatively, the controller 151 may incrementally increase the stimulation level of the excitation pulses 506 to increase the amplitude of the negative peak of the evoked potential waveform generated by the sensory fiber of the select dermatome.

Figure 14:
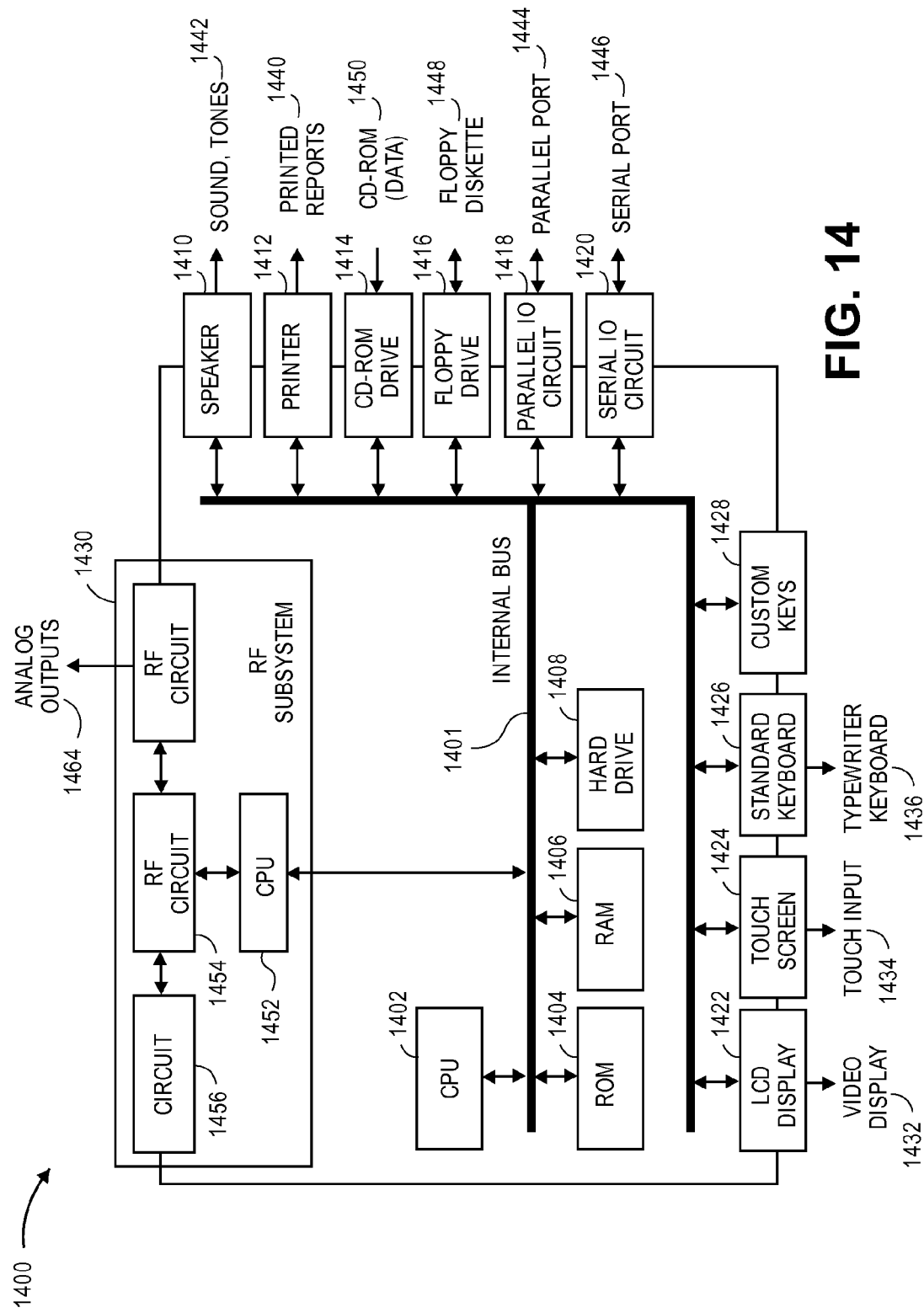
FIG. 14 illustrates a schematic block diagram of an external device, in accordance with an embodiment.

FIG. 14 illustrates a functional block diagram of an external device 1400, according to at least one embodiment, that is operated in accordance with the processes described herein and to interface with the NS system 100 as described herein. The external device 1400 may be similar to and/or the same as the external device 160. The external device 1400 may be a workstation, a portable computer, a tablet computer, a PDA, a cell phone and the like. The external device 1400 includes an internal bus 1401 that may connect/interface with a Central Processing Unit ("CPU") 1402, ROM 1404, RAM 1406, a hard drive 1408, a speaker 1410, a printer 1412, a CD-ROM drive 1414, a floppy drive 1416, a parallel I/O circuit 1418, a serial I/O circuit 1420, the display 1422, a touchscreen 1424, a standard keyboard 1426, custom keys 1428, and an RF subsystem 1430. The internal bus 1401 is an address/data bus that transfers information between the various components described herein. The hard drive 1408 may store operational programs as well as data, such as stimulation waveform templates and detection thresholds.

The CPU 1402 typically includes a microprocessor, a microcontroller, or equivalent control circuitry, designed specifically to control interfacing with the external device 1400 and with the NS system 100. The CPU 1402 may include RAM or ROM memory, logic and timing circuitry, state machine circuitry, and I/O circuitry to interface with the NS system 100. The display 1422 (e.g., may be connected to the video display 1432). The display 1422 displays various information related to the processes described herein. The touchscreen 1424 may display graphic information relating to the NS system 100 (e.g., stimulation levels, stimulation waveforms, evoked potential measurements) and include a graphical user interface. The graphical user interface may include graphical icons, scroll bars, buttons, and the like which may receive or detect user or touch inputs 1434 for the external device 1400 when selections are made by the user. Optionally the touchscreen 1424 may be integrated with the display 1422. The keyboard 1426 (e.g., a typewriter keyboard 1436) allows the user to enter data to the displayed fields, as well as interface with the RF subsystem 1430. Furthermore, custom keys 1428, for example, may turn on/off the external device 1400. The printer 1412 prints copies of reports 1440 for a physician to review or to be placed in a patient file, and the speaker 1410 provides an audible warning (e.g., sounds and tones 1442) to the user.

The parallel I/O circuit 1418 interfaces with a parallel port 1444. The serial I/O circuit 1420 interfaces with a serial port 1446. The floppy drive 1416 accepts diskettes 1448. Optionally, the serial I/O port may be coupled to a USB port or other interface capable of communicating with a USB device such as a memory stick. The CD-ROM drive 1414 accepts CD-ROMs 1450.

The RF subsystem 1430 includes a central processing unit (CPU) 1452 in electrical communication with RF circuitry 1454, which may communicate with both memory 1456 and an analog out circuit 1458. The analog out circuit 1458 includes communication circuits to communicate with analog outputs 1464. The external device 1400 may wirelessly communicate with the NS system 100 using a telemetry system. Additionally or alternatively, the external device 1400 may wirelessly communicate with the NS system 100 utilize wireless protocols, such as Bluetooth, Bluetooth low energy, WiFi, MICS, and the like. Alternatively, a hardwired connection may be used to connect the external device 1400 to the NS system 100.

Optionally, the external device 1400 may transmit the stimulation database request to the IPG 150. For example, the user may instruct the external device 1400 to transmit a stimulation database request from the graphical user interface on the touchscreen 1424, the keyboard 1426, or the like. The NS system 100 receives the request via the communication circuitry 155 (e.g., the RF subsystem 1430, RF circuitry 1454) and transmits the stimulation database stored on the memory 161 to the external device 900.

The controller 151, the CPU 1402, and the CPU 1452 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controller 151, the CPU 1402, and the CPU 1452 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controller 151, the CPU 1402, and the CPU 1452 may execute a set of instructions that are stored in one or more storage elements, in order to process data. The storage elements may also store data or other information as desired or needed. The storage element may be in the form of an information source or a physical memory element within the controller 151, the CPU 1402, and the CPU 1452. The set of instructions may include various commands that instruct the controller 151, the CPU 1402, and the CPU 1452 to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for closed loop spinal cord stimulation, the method comprising:
    positioning a first electrode proximate to a dorsal column, wherein the first electrode is electrically coupled to an implantable pulse generator (IPG);
    programming the IPG to deliver excitation pulses to the first electrode based on a stimulation level, wherein the excitation pulses are emitted from the first electrode;
    positioning a second electrode proximate to a dorsal root (DR), wherein the second electrode is electrically coupled to the IPG;
    measuring, at the second electrode, a first evoked potential waveform resulting from the excitation pulses; and
    determining from a morphology of the first evoked potential waveform activation of one or more sensory fiber types, wherein the one or more sensory fiber types are determined from peak latencies of the first evoked potential waveform.

2. The method of claim 1, wherein the first evoked potential waveform is measured from the second electrode which is located at a cell body of a dorsal root ganglia or a spinal nerve.

3. The method of claim 1, wherein the one or more sensory fiber types include at least a Aβ sensory fiber, Aδ sensory fiber, or a C sensory fiber.

4. The method of claim 1, further comprising adjusting the stimulation level based on the morphology of the first evoked potential waveform.

5. The method of claim 4, wherein adjusting the stimulation level changes at least one of an amplitude, polarity, pulse width, or a frequency of the excitation pulses delivered by the IPG.

6. The method of claim 1, wherein the morphology of the first evoked potential waveform includes at least one of a slope or a peak of the first evoked potential waveform during a predetermined time period.

7. The method of claim 6, wherein the predetermined time period depends on when the excitation pulses are emitted from the first electrode.

8. The method of claim 1, further comprising:
    adjusting the stimulation level based on a testing procedure; and
    iteratively repeating the measuring, determining, and adjusting operations until a therapeutic window is defined.

9. The method of claim 8, wherein the therapeutic window is defined based on activation of an Aδ sensory fiber or a C sensory fiber.

10. The method of claim 1, further comprising:
    positioning a third electrode proximate to a second DR or a contralateral DR corresponding to the DR, wherein the DR corresponds to a first dermatome and the second DR corresponds to a second dermatome; and
    measuring, at the third electrode, a second evoked potential waveform resulting from the excitation pulses.

11. The method of claim 1, further comprising repositioning a lead based on the morphology of the evoked potential waveform, wherein the lead includes the first electrode, the positioning operation of the first electrode corresponding to an intraoperative placement of the lead.

12. A system for closed loop spinal cord stimulation comprising:
    an implantable pulse generator (IPG) electrically coupled to a first electrode, wherein the IPG is configured to deliver excitation pukes to the first electrode based on a stimulation level;
    sensing circuitry of the IPG electric-ally coupled to a second electrode positioned proximate to a dorsal root (DR), wherein the sensing circuitry is configured to measure a first evoked potential waveform at the second electrode resulting from the excitation pulses; and
    a controller of the IPG that include one or more processors, the controller configured to determine from a morphology of the first evoked potential waveform activation of one or more sensory fiber types, wherein the one or more sensory fiber types are determined from peak latencies of the first evoked potential waveform.

13. The system of claim 12, further comprising a lead having the first electrode and the second electrode, wherein the first lead is coupled to the IPG.

14. The system of claim 12, further comprising:
    a first lead haying the first electrode, wherein the first lead is positioned proximate to a dorsal column; and
    a second lead having the second electrode, wherein the first lead and the second lead are coupled to the IPG.

15. The system of claim 12, wherein the controller is further configured to adjust the stimulation level based on the morphology of the first evoked potential waveform.

16. The system of claim 12, wherein the controller is further configured to adjust the stimulation level based on a testing procedure to define a therapeutic window.

17. The method of claim 16, wherein the therapeutic window is defined based on activation of an Aδ sensory fiber or a C sensory fiber.

\* \* \* \* \*